(12) United States Patent
Curro et al.

(10) Patent No.: US 7,682,686 B2
(45) Date of Patent: *Mar. 23, 2010

(54) TUFTED FIBROUS WEB

(75) Inventors: John Joseph Curro, Cincinnati, OH (US); Douglas Herrin Benson, West Harrison, IN (US); Daniel Charles Peck, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 161 days.

This patent is subject to a terminal disclaimer.

(21) Appl. No.: 11/156,020

(22) Filed: Jun. 17, 2005

(65) Prior Publication Data

US 2006/0286343 A1 Dec. 21, 2006

Related U.S. Application Data

(63) Continuation-in-part of application No. 10/737,306, filed on Dec. 16, 2003, which is a continuation-in-part of application No. 10/435,996, filed on May 12, 2003, now abandoned, which is a continuation-in-part of application No. 10/324,661, filed on Dec. 20, 2002, now abandoned, which is a continuation-in-part of application No. 10/737,430, filed on Dec. 16, 2003, which is a continuation-in-part of application No. 10/619,299, filed on Jun. 30, 2003, now abandoned.

(51) Int. Cl.
*B32B 3/00* (2006.01)
*B32B 5/14* (2006.01)

(52) U.S. Cl. .......................... 428/172; 428/85; 428/156; 428/171

(58) Field of Classification Search .................. 428/171, 428/172, 156–173, 131–140
See application file for complete search history.

(56) References Cited

U.S. PATENT DOCUMENTS 2,068,456 A 1/1937 Hooper
2,275,425 A 3/1942 Grabec (Continued)

FOREIGN PATENT DOCUMENTS

EP 0 509 012 B1 7/1995

(Continued)

OTHER PUBLICATIONS

PCT International Search Report dated Oct. 14, 2005.

(Continued)

*Primary Examiner*—Jenna-Leigh Johnson
(74) *Attorney, Agent, or Firm*—Andrew J. Hagerty; Gary J. Foose; Roddy M. Bullock

(57) ABSTRACT

A fibrous web having a first surface and a second surface. The fibrous web has a first region and at least one discrete second region, the second region being a discontinuity on the second surface and being a tuft comprising a plurality of tufted fibers extending from the first surface. The tufted fibers define a distal portion, the distal portion comprising portions of the tufted fibers being bonded together. Bonding can be thermal melt-bonding. In another embodiment the second surface of the web can have non-intersecting or substantially continuous bonded regions, which also can be thermal melt-bonding.

32 Claims, 12 Drawing Sheets

U.S. PATENT DOCUMENTS

| | | |
|---|---|---|
| 2,404,758 A | 7/1946 | Teague et al. |
| 2,633,441 A | 3/1953 | Buttress |
| 2,748,863 A | 6/1956 | Benton |
| 2,924,863 A | 2/1960 | Chavannes |
| 3,073,304 A | 1/1963 | Schaar |
| 3,081,500 A | 3/1963 | Griswold et al. |
| 3,081,512 A | 3/1963 | Griswold |
| 3,097,787 A | 7/1963 | Schur |
| 3,137,893 A | 6/1964 | Gelpke |
| 3,355,974 A | 12/1967 | Carmichael |
| 3,511,740 A | 5/1970 | Sanders |
| 3,542,634 A | 11/1970 | Such et al. |
| 3,566,726 A | 3/1971 | Politis |
| 3,579,763 A | 5/1971 | Sommer |
| 3,681,182 A | 8/1972 | Kalwaites |
| 3,681,183 A | 8/1972 | Kalwaites |
| 3,684,284 A | 8/1972 | Tranfield |
| 3,695,270 A | 10/1972 | Zdenek |
| 3,718,059 A | 2/1973 | Clayton |
| 3,760,671 A | 9/1973 | Jenkins |
| 3,881,987 A | 5/1975 | Benz |
| 3,949,127 A | 4/1976 | Ostermeier et al. |
| 3,965,906 A | 6/1976 | Karami |
| 4,035,881 A | 7/1977 | Zocher et al. |
| 4,042,453 A | 8/1977 | Conway |
| 4,135,021 A | 1/1979 | Patchell et al. |
| 4,276,336 A | 6/1981 | Sabee |
| 4,379,799 A | 4/1983 | Holmes |
| 4,397,644 A | 8/1983 | Matthews et al. |
| 4,465,726 A | 8/1984 | Holmes |
| 4,469,734 A | 9/1984 | Minto et al. |
| 4,588,630 A | 5/1986 | Shimalla |
| 4,596,567 A | 6/1986 | Iskra |
| 4,741,941 A | 5/1988 | Englebert et al. |
| 4,758,297 A | 7/1988 | Calligarich |
| 4,781,962 A | 11/1988 | Zamarripa et al. |
| 4,798,604 A | 1/1989 | Carter |
| 4,820,294 A | 4/1989 | Morris |
| 4,840,829 A | 6/1989 | Suzuki et al. |
| 4,859,519 A | 8/1989 | Cabe, Jr. et al. |
| 4,886,632 A | 12/1989 | Van Iten et al. |
| 4,935,087 A | 6/1990 | Gilman |
| 4,953,270 A | 9/1990 | Gilpatrick |
| 5,019,062 A | 5/1991 | Ryan et al. |
| 5,062,418 A | 11/1991 | Dyer |
| 5,144,730 A | 9/1992 | Dilo |
| 5,165,979 A | 11/1992 | Watkins et al. |
| 5,171,238 A | 12/1992 | Kajander |
| 5,180,620 A | 1/1993 | Mende |
| 5,188,625 A | 2/1993 | Van Iten et al. |
| 5,223,319 A | 6/1993 | Cotton et al. |
| 5,242,632 A | 9/1993 | Mende |
| 5,382,245 A | 1/1995 | Thompson |
| 5,383,870 A | 1/1995 | Takai et al. |
| 5,387,209 A | 2/1995 | Yamamoto et al. |
| 5,414,914 A | 5/1995 | Suzuki et al. |
| 5,415,640 A | 5/1995 | Kirby et al. |
| 5,429,854 A | 7/1995 | Currie et al. |
| 5,437,653 A | 8/1995 | Gilman et al. |
| 5,470,326 A | 11/1995 | Dabi et al. |
| 5,508,080 A | 4/1996 | Sorimachi et al. |
| 5,518,801 A | 5/1996 | Chappell et al. |
| 5,533,991 A | 7/1996 | Kirby et al. |
| 5,554,145 A | 9/1996 | Roe |
| 5,560,794 A | 10/1996 | Currie et al. |
| 5,567,501 A | 10/1996 | Srinivasan et al. |
| D375,844 S | 11/1996 | Edwards et al. |
| 5,573,719 A | 11/1996 | Fitting |
| 5,575,874 A * | 11/1996 | Griesbach et al. ............ 156/167 |
| 5,580,418 A | 12/1996 | Alikhan |
| 5,599,420 A | 2/1997 | Yeo et al. |
| 5,624,427 A | 4/1997 | Bergman et al. |
| 5,626,571 A | 5/1997 | Young et al. |
| 5,628,097 A | 5/1997 | Benson et al. |
| 5,648,142 A | 7/1997 | Phillips |
| 5,650,214 A | 7/1997 | Anderson et al. |
| 5,656,119 A | 8/1997 | Srinivasan et al. |
| 5,658,639 A | 8/1997 | Curro et al. |
| 5,667,619 A | 9/1997 | Alikhan |
| 5,667,625 A | 9/1997 | Alikhan |
| 5,691,035 A | 11/1997 | Chappell et al. |
| 5,700,255 A | 12/1997 | Curro |
| 5,704,101 A | 1/1998 | Majors et al. |
| 5,709,829 A | 1/1998 | Giacometti |
| 5,714,107 A | 2/1998 | Levy et al. |
| 5,723,087 A | 3/1998 | Chappell et al. |
| 5,725,927 A | 3/1998 | Zilg et al. |
| 5,730,738 A | 3/1998 | McFall et al. |
| 5,743,776 A | 4/1998 | Igaue |
| 5,792,404 A | 8/1998 | Cree et al. |
| 5,804,021 A | 9/1998 | Abuto et al. |
| 5,814,389 A | 9/1998 | Giacometti |
| 5,817,394 A | 10/1998 | Alikhan et al. |
| 5,841,107 A | 11/1998 | Riva |
| 5,858,504 A | 1/1999 | Fitting |
| 5,876,391 A | 3/1999 | Roe et al. |
| 5,879,494 A | 3/1999 | Hoff et al. |
| 5,891,544 A | 4/1999 | Chappell et al. |
| 5,895,623 A | 4/1999 | Trokhan et al. |
| 5,914,084 A | 6/1999 | Benson et al. |
| 5,916,661 A | 6/1999 | Benson et al. |
| 5,919,177 A | 7/1999 | Georger et al. |
| 5,925,026 A | 7/1999 | Arteman et al. |
| 5,932,316 A * | 8/1999 | Cree et al. .................. 428/182 |
| 5,964,742 A | 10/1999 | McCormack et al. |
| 5,968,029 A | 10/1999 | Chappell |
| 5,986,167 A | 11/1999 | Arteman et al. |
| 5,993,432 A | 11/1999 | Lodge et al. |
| 6,007,468 A | 12/1999 | Giacometti |
| 6,025,050 A | 2/2000 | Srinivasan et al. |
| 6,027,483 A | 2/2000 | Chappell et al. |
| 6,039,555 A | 3/2000 | Tsuji et al. |
| 6,048,600 A | 4/2000 | Hansson |
| 6,096,016 A | 8/2000 | Tsuji et al. |
| 6,114,263 A | 9/2000 | Benson et al. |
| 6,117,524 A | 9/2000 | Hisanaka et al. |
| 6,120,718 A | 9/2000 | Kotek et al. |
| 6,129,801 A | 10/2000 | Benson et al. |
| 6,155,083 A | 12/2000 | Goeser et al. |
| 6,168,849 B1 | 1/2001 | Braverman et al. |
| 6,176,954 B1 | 1/2001 | Tsuji et al. |
| 6,247,914 B1 | 6/2001 | Lindquist et al. |
| D444,631 S | 7/2001 | Woodbridge et al. |
| 6,264,872 B1 | 7/2001 | Majors et al. |
| 6,287,407 B1 | 9/2001 | Stein et al. |
| 6,383,431 B1 * | 5/2002 | Dobrin et al. ............... 264/154 |
| 6,395,122 B1 | 5/2002 | Hisanaka et al. |
| 6,395,211 B1 | 5/2002 | Dettmer et al. |
| 6,398,895 B1 | 6/2002 | Stein et al. |
| 6,410,823 B1 | 6/2002 | Daley et al. |
| 6,420,625 B1 | 7/2002 | Jones et al. |
| 6,423,884 B1 | 7/2002 | Oehmen |
| 6,451,718 B1 | 9/2002 | Yamada et al. |
| 6,452,064 B1 | 9/2002 | Thoren et al. |
| 6,458,447 B1 | 10/2002 | Cabell |
| D466,702 S | 12/2002 | Carlson et al. |
| 6,506,329 B1 | 1/2003 | Curro et al. |
| 6,537,936 B1 | 3/2003 | Busam et al. |
| 6,620,485 B1 | 9/2003 | Benson et al. |
| 6,632,504 B1 | 10/2003 | Gillespie et al. |
| D481,872 S | 11/2003 | Hennel et al. |
| 6,647,549 B2 | 11/2003 | McDevitt et al. |
| 6,669,878 B2 | 12/2003 | Yamada et al. |
| 6,716,498 B2 | 4/2004 | Curro et al. |

| | | | |
|---|---|---|---|
| 6,726,870 B1 | 4/2004 | Benson et al. | |
| 6,736,916 B2 | 5/2004 | Steinke et al. | |
| 6,794,626 B2 | 9/2004 | Copat et al. | |
| 6,808,791 B2 | 10/2004 | Curro et al. | |
| 6,818,802 B2 | 11/2004 | Takai et al. | |
| 6,830,800 B2 | 12/2004 | Curro et al. | |
| 6,837,956 B2 | 1/2005 | Cowell et al. | |
| 6,855,220 B2 | 2/2005 | Wildeman | |
| 6,863,960 B2 | 3/2005 | Curro et al. | |
| 6,872,274 B2 | 3/2005 | Kauschke et al. | |
| 6,878,433 B2 | 4/2005 | Curro et al. | |
| 6,884,494 B1 | 4/2005 | Curro et al. | |
| 7,005,558 B1 | 2/2006 | Johansson et al. | |
| 7,037,569 B2 | 5/2006 | Curro et al. | |
| 2002/0029445 A1 | 3/2002 | Laun et al. | |
| 2002/0039867 A1 | 4/2002 | Curro et al. | |
| 2002/0082574 A1 | 6/2002 | Nakashita | |
| 2002/0103469 A1 | 8/2002 | Chen et al. | |
| 2002/0105110 A1 | 8/2002 | Dobrin et al. | |
| 2002/0107495 A1 | 8/2002 | Chen et al. | |
| 2002/0119720 A1 | 8/2002 | Arora et al. | |
| 2002/0132544 A1 | 9/2002 | Takagaki | |
| 2003/0021951 A1 | 1/2003 | Desai et al. | |
| 2003/0028165 A1 | 2/2003 | Curro et al. | |
| 2003/0085213 A1 | 5/2003 | Burckhardt et al. | |
| 2003/0191442 A1 | 10/2003 | Bewick-Sonntag | |
| 2003/0191443 A1 | 10/2003 | Taylor | |
| 2004/0022993 A1 | 2/2004 | Wildeman | |
| 2004/0121686 A1 | 6/2004 | Wong et al. | |
| 2004/0122396 A1 | 6/2004 | Maldonado et al. | |
| 2004/0126531 A1 | 7/2004 | Harvey et al. | |
| 2004/0131820 A1 | 7/2004 | Turner et al. | |
| 2004/0137200 A1 | 7/2004 | Chhabra et al. | |
| 2004/0157036 A1 | 8/2004 | Provost et al. | |
| 2004/0161991 A1 | 8/2004 | Walton et al. | |
| 2004/0229008 A1 | 11/2004 | Hoying | |
| 2004/0242097 A1 | 12/2004 | Hasenoehrl et al. | |
| 2004/0265533 A1 | 12/2004 | Hoying et al. | |
| 2004/0265534 A1 | 12/2004 | Curro et al. | |
| 2005/0064136 A1 | 3/2005 | Turner et al. | |
| 2005/0096614 A1 | 5/2005 | Perez et al. | |
| 2005/0123726 A1 | 6/2005 | Broering et al. | |
| 2005/0281976 A1 | 12/2005 | Curro et al. | |
| 2005/0283129 A1 | 12/2005 | Hammons et al. | |
| 2006/0019056 A1 | 1/2006 | Turner et al. | |
| 2006/0087053 A1 | 4/2006 | O'Donnell et al. | |
| 2006/0286343 A1 | 12/2006 | Curro et al. | |

FOREIGN PATENT DOCUMENTS

| | | | |
|---|---|---|---|
| EP | 0 955 159 A1 | 11/1999 | |
| EP | 0 963 747 A1 | 12/1999 | |
| EP | 1 004 412 A1 | 5/2000 | |
| FR | 2 713 083 A1 | 6/1995 | |
| FR | 2713083 A1 | 6/1995 | |
| WO | WO 95/15138 | 6/1995 | |
| WO | WO 01/76523 A2 | 10/2001 | |
| WO | WO 02/100632 A1 | 12/2002 | |
| WO | WO 2005/011936 A1 | 2/2005 | |

OTHER PUBLICATIONS

Office Action for U.S. Appl. No. 12/370,850 dated Jul. 8, 2009; Turner et al., filed Feb. 13, 2009.
Office Action for U.S. Appl. No. 11/158,165 dated May 16, 2008; Turner et al., filed Jun. 21, 2005.
Office Action for U.S. Appl. No. 11/158,165 dated Dec. 7, 2007; Turner et al., filed Jun. 21, 2005.
Office Action for U.S. Appl. No. 11/158,165 dated Jul. 3, 2007; Turner et al, filed Jun. 21, 2005.
Office Action for U.S. Appl. No. 11/157,770 dated Apr. 28, 2009; Hammons et al., filed Jun. 21, 2005.
Office Action for U.S. Appl. No. 11/157,770 dated Jun. 2, 2008; Hammons et al., filed Jun. 21, 2005.
Office Action for U.S. Appl. No. 11/157,770 dated Oct. 1, 2007; Hammons et al., filed Jun. 21, 2005.
Examiner's Answer for U.S. Appl. No. 11/155,805 dated Aug. 6, 2009; Curro et al., filed Jun. 17, 2005.
Office Action for U.S. Appl. 11/155,805 dated Oct. 30, 2008; Curro et al., filed Jun. 17, 2005.
Office Action for U.S. Appl. No. 11/155,805 dated May 16, 2008; Curro et al., filed Jun. 17, 2005.
Office Action for U.S. Appl. No. 11/155,805 dated Nov. 27, 2007; Curro et al., filed Jun. 17, 2005.
Office Action for U.S. Appl. No. 11/155,805 dated Jun. 19, 2007; Curro et al., filed Jun. 17, 2005.
Office Action for U.S. Appl. No. 10/737,235 dated May 6, 2009; Hoying et al., filed Dec. 16, 2003.
Office Action for U.S. Appl. No. 10/737,235 dated Nov. 25, 2008; Hoying et al., filed Dec. 16, 2003.
Office Action for U.S. Appl. No. 10/737,235 dated Jun. 12, 2008; Hoying et al., filed Dec. 16, 2003.
Office Action for U.S. Appl. No. 10/737,235 dated Dec. 12, 2007; Hoying et al., filed Dec. 16, 2003.
Office Action for U.S. Appl. No. 10/737,235 dated Jul. 26, 2007; Hoying et al., filed Dec. 16, 2003.
Office Action for U.S. Appl. No. 10/737,235 dated Feb. 6, 2007; Hoying et al., filed Dec. 16, 2003.
Office Action for U.S. Appl. No. 10/737,235 dated Aug. 8, 2006; Hoying et al., filed Dec. 16, 2003.
Office Action for U.S. Appl. No. 10/737,235 dated Feb. 3, 2006; Hoying et al., filed Dec. 16, 2003.
Office Action for U.S. Appl. No. 10/737,235 dated Aug. 24, 2005; Hoying et al., filed Dec. 16, 2003.
Office Action for U.S. Appl. No. 11/650,821 dated Mar. 16, 2009; Hoying et al., filed date Jan. 8, 2007.
Office Action for U.S. Appl. No. 11/650,821 dated Oct. 8, 2008; Hoying et al., filed Jan. 8, 2007.
Office Action for U.S. Appl. No. 11/650,821 dated Apr. 23, 2008; Hoying et al., filed Jan. 8, 2007.
Office Action for U.S. Appl. No. 11/650,821 dated Oct. 16, 2007; Hoying et al., filed Jan. 8, 2007.
Notice of Allowance for U.S. Appl. No. 10/737,307 dated Sep. 28, 2006; Hoying et al., filed Dec. 16, 2003.
Office Action for U.S. Appl. No. 10/737,307 dated May 31, 2006; Hoying et al., filed Dec. 16, 2003.
Office Action for U.S. Appl. No. 10/737,307 dated Oct. 7, 2005; Hoying et al., filed Dec. 16, 2003.
Notice of Allowance for U.S. Appl. No. 10/980,219 dated May 23, 2007; Broering et al., filed Nov. 3, 2004.
Office Action for U.S. Appl. No. 10/980,219 dated Mar. 5, 2007; Broering et al., filed Nov. 3, 2004.
Office Action for U.S. Appl. No. 10/980,219 dated Sep. 11, 2006; Broering et al., filed Nov. 3, 2004.
Notice of Allowance for U.S. Appl. No. 10/737,430 dated Mar. 18, 2008; Curro et al., filed Dec. 16, 2003.
Notice of Allowance for U.S. Appl. No. 10/737,430 dated Oct. 29, 2007; Curro et al., filed Dec. 16, 2003.
Office Action for U.S. Appl. No. 10/737,430 dated Jul. 16, 2007; Curro et al., filed Dec. 16, 2003.
Office Action for U.S. Appl. No. 10/737,430 dated Jan. 25, 2007; Curro et al., filed Dec. 16, 2003.
Office Action for U.S. Appl. No. 10/737,430 dated Aug. 8, 2006; Curro et al., filed Dec. 16, 2003.
Office Action for U.S. Appl. No. 10/737,430 dated Feb. 3, 2006; Curro et al., filed Dec. 16, 2003.
Office Action for U.S. Appl. No. 10/737,430 dated 8/24/05; Curro et al., filed Dec. 16, 2003.
Office Action for U.S. Appl. No. 12/021,369 dated Jun. 25, 2009; Curro et al., filed Jan. 29, 2008.
Office Action for U.S. Appl. No. 10/737,306 dated Jun. 12, 2008; Gray et al., filed Mar. 28, 2003.
Notice of Allowance for U.S. Appl. No. 10/737,306 dated Nov. 29, 2007; Gray et al., filed Mar. 28, 2003.
Office Action for U.S. Appl. No. 10/737,306 dated Jul. 16, 2007; Gray et al., filed Mar. 28, 2003.

Office Action for U.S. Appl. No. 10/737,306 dated Jan. 26, 2007; Gray et al., filed Mar. 28, 2003.

Office Action for U.S. Appl. No. 10/737,306 dated Aug. 9, 2006; Gray et al., filed Mar. 28, 2003.

Office Action for U.S. Appl. No. 10/737,306 dated Aug. 24, 2005; Gray et al., filed Mar. 28, 2003.

Office Action for U.S. Appl. No. 10/737,306 dated Feb. 3, 2006; Gray et al., filed Mar. 28, 2003.

Office Action for U.S. Appl. No. 11/129,877 dated Mar. 30, 2007; Cabell, filed May 16, 2005.

Office Action for U.S. Appl. No. 11/129,877 dated Oct. 2, 2007; Cabell, filed May 16, 2005.

Office Action for U.S. Appl. No. 11/129,877 dated Jan. 23, 2008; Cabell, filed May 16, 2005.

Office Action for U.S. Appl. No. 11/129,877 dated Jun. 12, 2008; Cabell, filed May 16, 2005.

* cited by examiner

TUFTED FIBROUS WEB

CROSS-REFERENCE TO RELATED APPLICATIONS

This application is a continuation-in-part of U.S. application Ser. No. 10/737,306, filed Dec. 16, 2003, which is a continuation-in-part of U.S. application Ser. No. 10/435,996, filed May 12, 2003, now abandoned, which is a continuation-in-part of U.S. application Ser. No. 10/324,661, filed Dec. 20, 2002, now abandoned. This application is a continuation-in-part of U.S. application Ser. No. 10/737,430, filed Dec. 16, 2003, which is a continuation-in-part of U.S. application Ser. No. 10/610,299, filed Jun. 30, 2003, now abandoned.

FIELD OF INVENTION

This invention relates to fibrous webs such as woven and nonwoven webs. In particular, this invention relates to fibrous webs treated by mechanical formation to have increased softness or bulk properties.

BACKGROUND OF THE INVENTION

Fibrous webs are well known in the art. For example, woven webs such as textile and knit fabrics are well known as material for clothing, upholstery, drapes, and the like. Also, nonwoven webs such as webs formed from polymer fibers are well known as materials useful for disposable products such as facing layers on absorbent articles such as diapers, for example.

In many applications it is desirable that fibrous webs have a bulky texture and/or softness. Also, due to cost limitations, many commercial uses for nonwovens in disposable absorbent products also demand that minimal amounts of material be used. Therefore, there is a continuing demand for technologies and materials capable of producing low basis weight, bulky and soft nonwovens. One very effective way is disclosed in commonly-owned, U.S. application Ser. Nos. 10/737,306 and 10/737,430 each of which describes nonwoven webs having tufts.

However, there is a continuing need for a low cost fibrous web having soft, bulky properties.

Additionally, there is a need for a method for relatively inexpensively making a fibrous web having soft, bulky properties.

Further, there is a need for a low cost method of making a soft, porous web of woven or nonwoven material that can be commercially used in disposable consumer products.

SUMMARY OF THE INVENTION

A fibrous web having a first surface and a second surface is disclosed. The fibrous web has a first region and at least one discrete second region, the second region being a discontinuity on the second surface and being a tuft comprising a plurality of tufted fibers extending from the first surface. The tufted fibers define a distal portion, the distal portion comprising portions of the tufted fibers being bonded together. Bonding can be thermal melt-bonding. In another embodiment the second surface of the web can have non-intersecting or substantially continuous bonded regions, which also can be thermal melt-bonding.

DETAILED DESCRIPTION OF THE INVENTION

Figure 1:
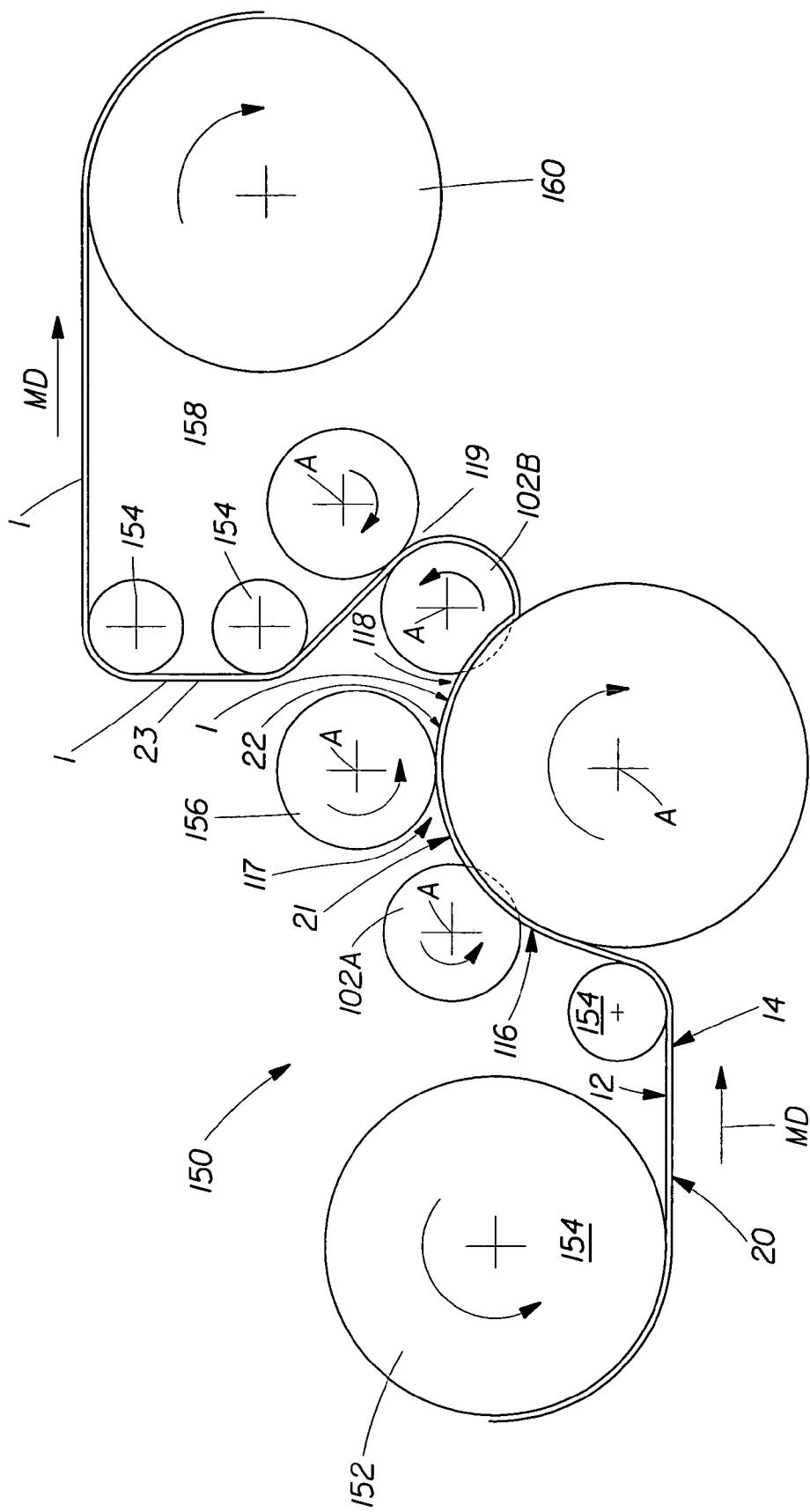
FIG. 1 is a schematic representation of an apparatus for making a web of the present invention.

A web 1 of the present invention will be described with respect to a preferred method and apparatus of making. A preferred apparatus 150 of the present invention is shown schematically in FIG. 1. As shown in FIG. 1, web 1 can be formed from a generally planar, two dimensional nonwoven precursor web 20 having a first surface 12 and a second surface 14. Precursor web 20 can be can be, for example, a polymer film, a nonwoven web, a woven fabric, a paper web, a tissue paper web, or a knitted fabric.

For nonwoven precursor webs 20, the precursor web can comprise unbonded fibers, entangled fibers, tow fibers, or the like, as is known in the art for nonwoven webs. Fibers can be extensible and/or elastic, and may be pre-stretched for processing by apparatus 150. Fibers of precursor web 20 can be continuous, as those produced by spunbonded methods, or cut to length, such as those typically utilized in a carded process. Fibers can be absorbent, and can include fibrous absorbent gelling materials (fibrous AGM). Fibers can be bicomponent, multiconstituent, shaped, crimped, or in any other formulation or configuration known in the art for nonwoven webs and fibers.

Precursor web 20 can be a composite or a laminate of two or more precursor webs, and can comprise, for example, two or more nonwoven webs or a combination of polymer films, nonwoven webs, woven fabrics, paper webs, tissue webs, or knitted fabrics. Precursor web 20 can be supplied from a supply roll 152 (or supply rolls, as needed for multiple web laminates) or any other supply means, such as festooned webs, as is known in the art. In one embodiment, precursor web 20 can be supplied directly from a web making apparatus, such as a nonwoven web-making production line. Precursor web 20 is moved in a machine direction (MD) for forming by apparatus 150 into web 1 of the present invention.

Machine direction (MD) refers to the direction of travel for precursor web 20 as is commonly known in the art of making or processing web materials. Likewise, cross machine direction (CD) refers to a direction perpendicular to the MD, in the plane of precursor web 1.

First surface 12 corresponds to first side of precursor web 20, as well as the first side of web 1. Second surface 14 corresponds to the second side of precursor web 20, as well of web 1. In general, the term "side" is used herein in the common usage of the term to describe the two major surfaces of generally two-dimensional webs, such as paper and films. Of course, in a composite or laminate structure, the first surface 12 of the web 1 is the first side of one of the outermost webs, and the second surface 14 is the second side of the other outermost web.

To make fibrous webs 1 or laminates of webs 1, the method of the present invention can be practiced with woven and knitted fabrics. However, in a preferred embodiment precursor web (or webs) 20 is a nonwoven web and is comprised of substantially randomly oriented fibers, that is, randomly oriented at least with respect to the MD and CD. By "substantially randomly oriented" is meant random orientation that, due to processing conditions, may exhibit a higher amount of fibers oriented in the MD than the CD, or vice-versa. For example, in spunbonding and meltblowing processes continuous strands of fibers are deposited in a random orientation on a support moving in the MD. Despite attempts to make the orientation of the fibers of the spunbond or meltblown nonwoven web truly "random," usually a higher percentage of fibers are oriented in the MD as opposed to the CD.

In some embodiments of the present invention it may be desirable to purposely orient a significant percentage of fibers in a predetermined orientation with respect to the MD in the plane of the web. For example, it may be that, due to tooth spacing and placement on roll 104 (as discussed below), it may be desirable to produce a nonwoven web having a predominant fiber orientation at an angle of, for example, 60 degrees off parallel to the longitudinal axis of the web. Such webs can be produced by processes that combine lapping webs at the desired angle, and, if desired carding the web into a finished web. A web having a high percentage of fibers having a predetermined angle can statistically bias more fibers to be formed into tufts in web 1, as discussed more fully below.

Nonwoven precursor webs 20 can be any known nonwoven webs comprising polymer fibers having sufficient elongation properties to be formed into web 1 as described more fully below. In general, the polymeric fibers can be bondable, either by chemical bond, i.e., by latex or adhesive bonding, pressure bonding, or thermal bonding. If thermal bonding techniques are used in the bonding process described below, a certain percentage of thermoplastic material, such as thermoplastic powder or fibers can be utilized as necessary to facilitate thermal bonding of portions of fibers in the web, as discussed more fully below. Nonwoven precursor web 20 can comprise 100% by weight thermoplastic fibers, but it can comprise as low as 10% by weight thermoplastic fibers. Likewise, nonwoven precursor web 20 can comprise any amount by weight thermoplastic fibers in 1% increments between about 10% and 100%.

As used herein, the term "nonwoven web" refers to a web having a structure of individual fibers or threads which are interlaid, but not in a repeating pattern as in a woven or knitted fabric, which do not have randomly oriented fibers. Nonwoven webs or fabrics have been formed from many known processes, such as, for example, air laying processes, meltblowing processes, spunbonding processes, hydroentangling processes, spunlacing processes, and bonded carded web processes. Also, multi-layer webs, such as spunbond-meltblown-spunbond (SMS) webs and the like (e.g., SMMS, SSMS) made by multiple beam spunbond processes, can be utilized. It is not necessary that each component (i.e., the spunbond or meltblown components) be the same polymer. Therefore, in an SMS web, it is not necessary that the spunbond and the meltblown layers comprise the same polymer.

The basis weight of nonwoven fabrics is usually expressed in grams per square meter (gsm) (or equivalent, such as oz/sq yard) and the fiber diameters are usually expressed in microns. Fiber size can also be expressed in denier. The total basis weight of precursor web 20 (including laminate or multi-layer precursor webs 20) can range from 8 gsm to 500 gsm, depending on the ultimate use of the web 1, and can be produced in 1 gsm increments between 8 and 500 gsm. For use as a hand towel, for example, a basis weight of precursor web 20 of between 25 gsm and 100 gsm may be appropriate. For use as a bath towel a basis weight of between 125 gsm and 250 gsm may be appropriate. For use as an air filter, including a High Efficiency Particulate Air (HEPA) filter, useful in air cleaning equipment including dust collectors, nuclear and biological filters, and some types of gas turbine inlet air filtration, a basis weight of between 350 gsm and 500 gsm may be appropriate (pleated and ganged, if necessary to increase effective surface area). The constituent fibers of nonwoven precursor web 20 can be polymer fibers, and can be monocomponent, bicomponent and/or biconstituent fibers, hollow fibers, non-round fibers (e.g., shaped (e.g., trilobal) fibers or capillary channel fibers), and can have major cross-sectional dimensions (e.g., diameter for round fibers, long axis for elliptical shaped fibers, longest straight line dimension for irregular shapes) ranging from 0.1-500 microns in 1 micron increments.

As used herein, "spunbond fibers" is used in its conventional meaning, and refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" is used in its conventional meaning, and refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" is used in its conventional meaning, and generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries. In general, any of the known polymer types can be utilized in the present invention, for example, polyolefinic polymers such as polypropylene or polyethylene can be used either as monocomponent fibers or bicomponent fibers. Additionally, other polymers such as PVA, PET polyesters, metallocene catalyst elastomers, and blends thereof can be used, any or all of which polymers can be cross linked if desired.

As used herein, the term "monocomponent" fiber is used in its conventional meaning, and refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" is used in its conventional meaning, and refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer (such as polypropylene) is surrounded by another (such as polyethylene), or may be a side-by-side arrangement, a pie arrangement, or an "islands-in-the-sea" arrangement, each as is known in the art of multicomponent, including bicomponent, fibers.

Fibers, including bicomponent fibers, can be splittable fibers, such fibers being capable of being split lengthwise before or during processing into multiple fibers each having a smaller cross-sectional dimension than the original bicomponent fiber. Splittable fibers have been shown to produce softer nonwoven webs due to their reduced cross-sectional dimensions. Fibers can be nanofibers, i.e., fibers having a diameter in the sub-micron range up to and including the low micron range.

As used herein, the term "biconstituent fibers" is used in its conventional meaning, and refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, the term "non-round fibers" is used in its conventional meaning, and describes fibers having a non-round cross-section, and include "shaped fibers" and "capillary channel fibers." Such fibers can be solid or hollow, and they can be tri-lobal, delta-shaped, and are preferably fibers having longitudinally-extending grooves that serve as capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T401 fiber is a polyethylene terephthalate (PET polyester).

Unless otherwise noted, all other terms are used in their conventional, ordinary meaning as used by those skilled in the art.

Precursor web 20 can be provided either directly from a web making process or indirectly from a supply roll 152, as shown in FIG. 1. Precursor web 20 can be preheated by means known in the art, such as by heating over oil-heated rollers. Precursor web 20 can be pre-printed with indicia, designs, logos, or other visible or invisible print pattern. For example, designs and colors can be printed by means known in the art, such as by ink-jet printing, gravure printing, or offset printing, to change the color of at least portions of precursor web 20. In addition to printing, precursor web 20 can be treated with coatings, such as with surfactants, lotions, adhesives, and the like. Treating precursor web 20 can be achieved by means known in the art such as by spraying, slot coating, extruding, or otherwise applying coatings to one or both surfaces.

Supply roll 152 rotates in the direction indicated by the arrow as precursor web 20 is moved in the machine direction over roller 154 and to the nip 116 of a first set of counter-rotating intermeshing rolls 102A and 104. Rolls 102A and 104 are the first set of intermeshing rollers of apparatus 150. The first set of intermeshing rolls 102A and 104 operate to form tufts in web 1, to make tufted precursor web 21. Intermeshing rolls 102A and 104 are more clearly shown in FIG. 2.

Figure 2:
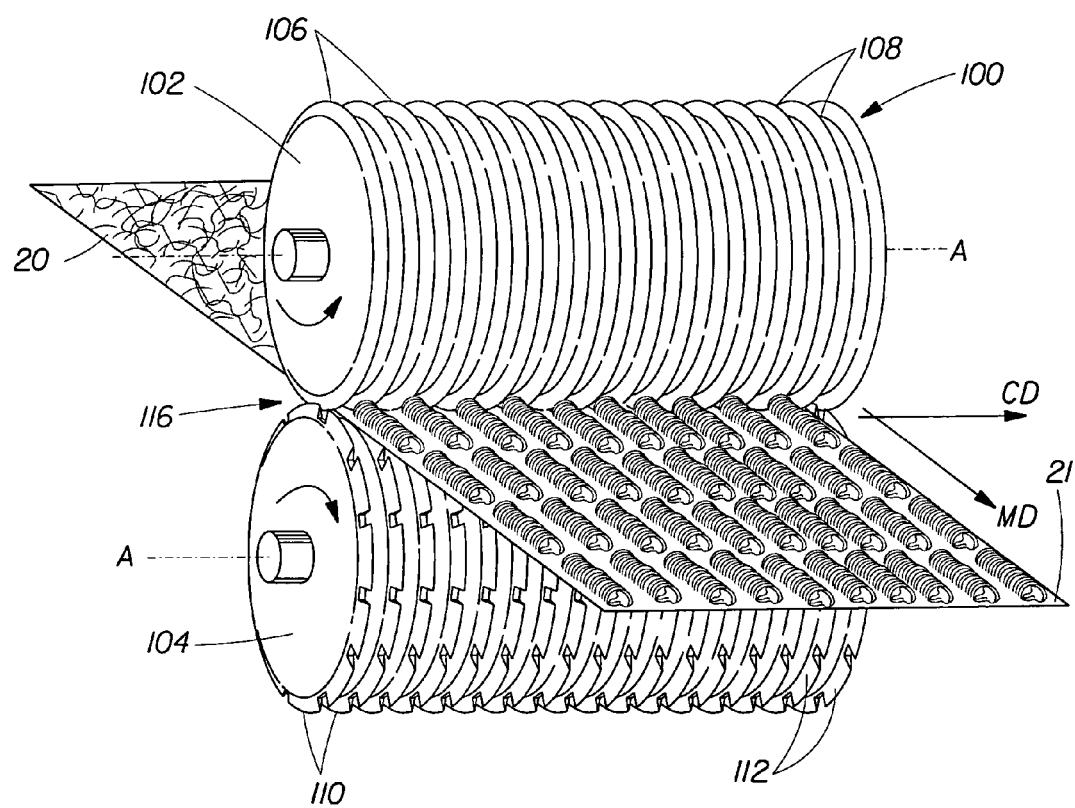
FIG. 2 is an enlarged view of a portion of the apparatus shown in FIG. 1.

Referring to FIG. 2, there is shown in more detail the portion of apparatus 150 for making tufts on tufted precursor web 21 of the present invention. This portion of apparatus 150 is shown as nip rollers 100 in FIG. 2, and comprises a pair of steel intermeshing rolls 102 and 104 (corresponding to rolls 102A and 104, respectively, in FIG. 1), each rotating about an axis A, the axes A being parallel in the same plane. Although the apparatus 150 is designed such that precursor web 20 remains on roll 104 through a certain angle of rotation, FIG. 2 shows in principle what happens as precursor web 20 goes through nip 116 on apparatus 150 an exits as tufted precursor web 21. Therefore, while FIG. 2 shows tufted precursor web 21 coming straight out of nip 116, on apparatus 150 tufted precursor web 21 can continue on roll 104 through a predetermined angle of rotation such that the tufts remain resting over, and "fitted" onto, teeth 110 of roll 104.

Roll 102 comprises a plurality of ridges 106 and corresponding grooves 108 which can extend unbroken about the entire circumference of roll 102. In some embodiments, depending on what kind of pattern is desired in precursor web 21, roll 102 (and, likewise, roll 102A) can comprise ridges 106 wherein portions have been removed, such as by etching, milling or other machining processes, such that some or all of ridges 106 are not circumferentially continuous, but have breaks or gaps. The breaks or gaps can be arranged to form a pattern, including simple geometric patters such as circles or diamonds, but also including complex patterns such as logos and trademarks. In one embodiment, roll 102 can have teeth, similar to the teeth on roll 104, described more fully below. In this manner, it is possible to have tufts on both sides of tufted precursor web 21. In addition to tufts, various out-of-plane macro-areas of tufts of web 21 can be made, including macro-patterns depicting logos and/or designs.

Roll 104 is similar to roll 102, but rather than having ridges that can extend unbroken about the entire circumference, roll 104 comprises a plurality of rows of circumferentially-extending ridges that have been modified to be rows of circumferentially-spaced teeth 110 that extend in spaced relationship about at least a portion of roll 104. The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the grooves 108 of roll 102. The intermeshing is shown in greater detail in the cross sectional representation of FIG. 7, discussed below. Both or either of rolls 102 and 104 can be heated by means known in the art such as by using hot oil filled rollers or electrically-heated rollers.

A portion of tufted precursor web 21 is shown in FIGS. 3-6. As shown, tufted precursor web 21 has a first region 2 defined on both sides of tufted precursor web 21 by the generally planar, two-dimensional configuration of the precursor web 20, and a plurality of discrete second regions 4 defined by spaced-apart tufts 6 and discontinuities 16 which can result from integral extensions of the fibers of the precursor web 20. The structure of second regions 4 is differentiated depending on which side of tufted precursor web 21 is considered. For the embodiment of tufted precursor web 21 shown in FIG. 3, on the side of tufted precursor web 21 associated with first surface 12 of tufted precursor web 21, second regions 4 comprise tufts 6, and each tuft 6 can comprise a plurality of tufted, looped, aligned fibers 8 extending outwardly from first surface 12. Tufts 6 comprise tufts of fibers having a significant orientation in the Z-direction, and each tuft 6 has a base 5 proximal to the first surface 12, and a distal portion 3 at a maximum distance in the Z-direction from the first surface 12. On the side of tufted precursor web 21 associated with second surface 14, second region 4 comprises discontinuities 16 which are defined by fiber orientation discontinuities 16 on the second surface 14 of tufted precursor web 21, the discontinuities 16 corresponding to the locations where teeth 110 of roll 104 penetrated precursor web 20. As shown below, in other embodiments of tufted precursor web 21, it is possible that the tufts 6 not comprise looped or aligned fibers.

As used herein, the term "integral" as in "integral extension" when used of the second regions 4 refers to fibers of the second regions 4 having originated from the fibers of the precursor web 20. Therefore, the looped fibers 8 of tufts 6, for example, can be plastically deformed and/or extended fibers of the precursor web 20, and can be, therefore, integral with first regions 2 of tufted precursor web 21. As used herein, "integral" is to be distinguished from fibers introduced to or added to a separate precursor web for the purpose of making tufts, as is commonly done in conventional carpet making, for example. While some embodiments of web 1 of the present invention may utilize such added fibers, in a preferred embodiment, fibers of tufts 6 are integral to web 1.

It can be appreciated that a suitable precursor web 20 for a web 1 of the present invention having looped fibers in tufts 6 should comprise fibers capable of experiencing sufficient fiber mobility and/or plastic deformation and tensile elongation such that looped fibers 8 are formed. However, it is recognized that a certain percentage of fibers urged out of the plane of the first surface 12 of precursor web 20 will not form a loop, but instead will break and form loose ends. Such fibers are shown as loose fiber ends 18 in FIGS. 4 and 5. Loose fiber ends 18 are not necessarily undesirable for the present invention, but it is believed that web 1 can retain its bulky and soft character more readily when tuft 6 comprises primarily looped fibers 8. In a preferred embodiment at least 50%, more preferably at least 70% and more preferably at least 90% of the fibers urged in the Z-direction are looped fibers 8.

A representative tuft 6 for the embodiment of tufted precursor web 21 shown in FIG. 2 is shown in a further enlarged view in FIGS. 3-6. The representative tuft 6 is of the type formed on an elongated tooth 110 on roll 104, such that the tuft 6 comprises a plurality of looped fibers 8 that are substantially aligned such that tuft 6 has a distinct longitudinal orientation and a longitudinal axis L. Tufts 6 also have a transverse axis T generally orthogonal to longitudinal axis L in the MD-CD plane. In the embodiment shown in FIGS. 2-6, longitudinal axis L is parallel to the MD. In one embodiment, all the spaced apart tufts 6 have generally parallel longitudinal axes L. While in preferred embodiments tufts 6 will have a longitudinal orientation, in some embodiments such an orientation may not be present. For example, if teeth 110 on roll 104 have a length on the tufts 6 may not display any longitudinal orientation.

The number of tufts 6 per unit area of tufted precursor web 21, i.e., the area density of tufts 6, can be varied from 1 tuft 6 per square centimeter to as high as 30 tufts 6 per square centimeter. There can be at least 10, or at least 20 tufts 6 per square centimeter, depending on the end use. In general, the area density need not be uniform across the entire area of precursor web 21, but tufts 6 can be only in certain regions of tufted precursor web 21, such as in regions having predetermined shapes, such as lines, stripes, bands, circles, and the like.

Figure 4:
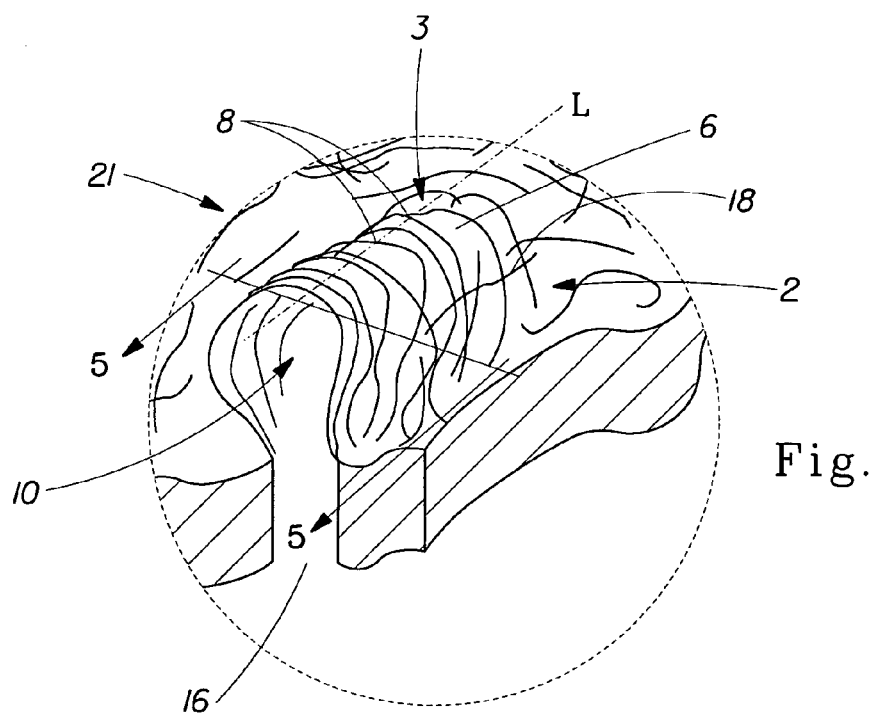
FIG. 4 is an enlarged portion of the web shown in FIG. 3.
Figure 5:
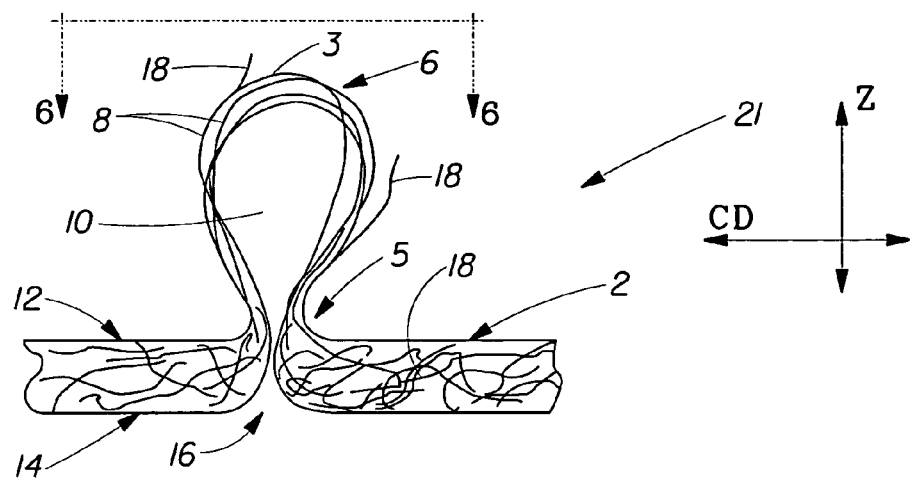
FIG. 5 is a cross-sectional view of a portion of the web shown in FIG. 4.
Figure 6:
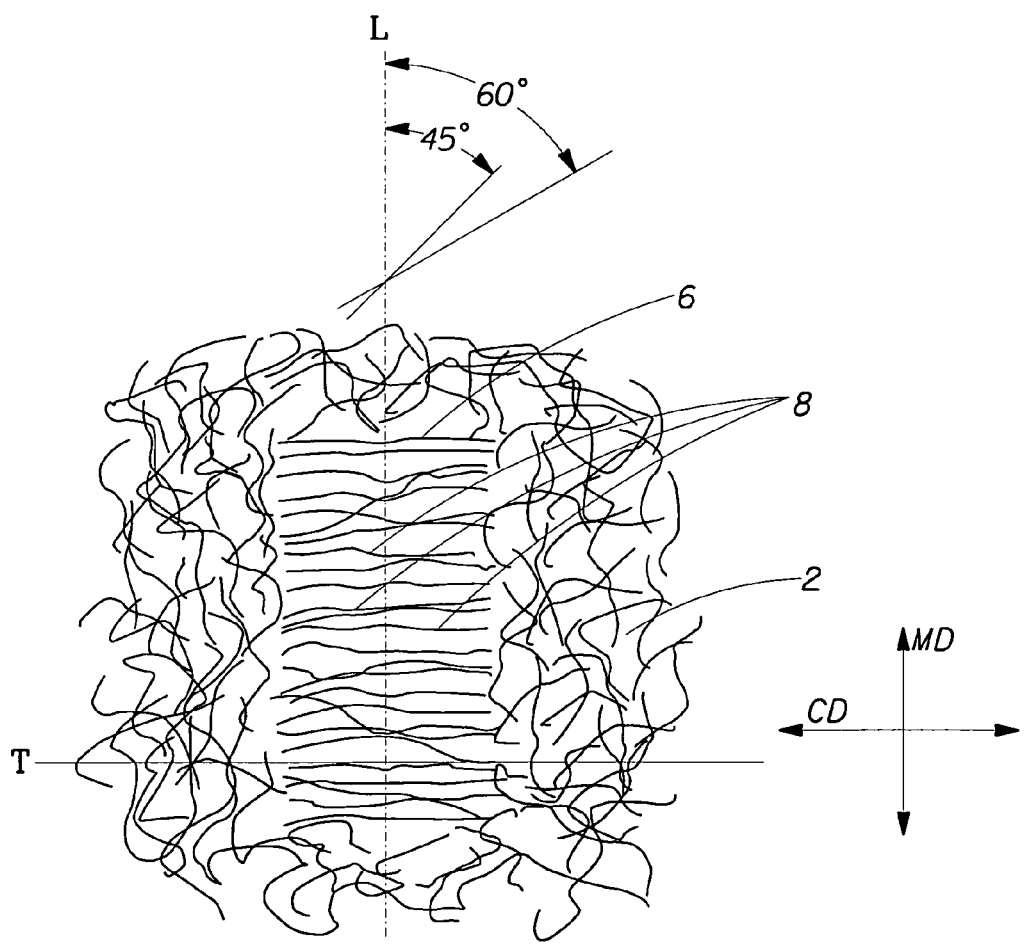
FIG. 6 is a plan view of a portion of the web shown in FIG. 5.

As shown in FIG. 4, and more clearly in FIGS. 5 and 6, when elongated teeth 110 are utilized on roll 104, one characteristic of the fibers 8 of tufts 6 in one embodiment of tufted precursor web 21 is the predominant directional alignment of the looped fibers 8. As shown in FIGS. 5 and 6, many of looped fibers 8 can have a substantially uniform alignment with respect to transverse axis T when viewed in plan view, such as in FIG. 6. By "looped" fibers 8 is meant that fibers 8 begin and end in tufted precursor web 21. By "aligned" with respect to looped fibers 8 of tufts 6 is meant that looped fibers 8 are generally oriented such that, if viewed in plan view as in FIG. 6, the looped fibers 8 have a significant vector component parallel to the transverse axis T, and preferably a major vector component parallel to the transverse axis T. As used herein, a looped fiber 8 oriented at an angle of greater than 45 degrees from the longitudinal axis L when viewed in plan view, as in FIG. 6, has a significant vector component parallel to the transverse axis T. As used herein, a looped fiber 8 oriented at an angle of greater than 60 degrees from longitudinal axis L when viewed in plan view, as in FIG. 6, has a major vector component parallel to the transverse axis T. In a preferred embodiment, at least 50%, more preferably at least 70%, and more preferably at least 90% of fibers 8 of tuft 6 have a significant, and more preferably, a major, vector component parallel to transverse axis T. Fiber orientation can be determined by use of magnifying means if necessary, such as a microscope fitted with a suitable measurement scale. In general, for a non-linear segment of fiber viewed in plan view, a straight-line approximation for both longitudinal axis L and the looped fibers 8 can be used for determining the angle of looped fibers 8 from longitudinal axis L.

The orientation of looped fibers 8 in the tufts 6 of second region 4 is to be contrasted with the fiber composition and orientation of the first region 2, which, for nonwoven precursor webs 20 is best described as having a substantially randomly-oriented fiber alignment. In a woven web embodiment, the orientation of the looped fibers 8 in tufts 6 could be the same as described above, but the fibers of second region 2 would have the orientation associated with the particular weaving process used to make the web, e.g., a square weave pattern.

In the embodiment shown in FIG. 2 the longitudinal axes L of tufts 6 are generally aligned in the MD. Tufts 6 and, therefore, longitudinal axes L, can, in principle, be aligned in any orientation with respect to the MD or CD, with corresponding modifications to rolls 102A and 104. Therefore, in general, it can be said that for each tuft 6, the looped aligned fibers 8 are aligned generally orthogonal to the longitudinal axis L such that they have a significant vector component parallel to transverse axis T, and more preferably a major vector component parallel to transverse axis T.

As can be understood with respect to apparatus 150, therefore, tufts 6 of tufted precursor web 20 are made by mechanically deforming precursor web 20 that can be described as generally planar and two dimensional. By "planar" and "two dimensional" is meant simply that the web is flat relative to the finished web 1 that has distinct, out-of-plane, Z-direction three-dimensionality imparted due to the formation of second regions 4. "Planar" and "two-dimensional" are not meant to imply any particular flatness, smoothness or dimensionality. As precursor web 20 goes through the nip 116 the teeth 110 of roll 104 enter grooves 108 of roll 102A and simultaneously urge fibers out of the plane of precursor web 20 to form second regions 4, including tufts 6 and discontinuities 16. In effect, teeth 110 "push" or "punch" through precursor web 20. As the tip of teeth 110 push through precursor web 20 the portions of fibers that are oriented predominantly in the CD and across teeth 110 are urged by the teeth 110 out of the plane of precursor web 20 and are stretched, pulled, and/or plastically deformed in the Z-direction, resulting in formation of second region 4, including the looped fibers 8 of tufts 6. Fibers that are predominantly oriented generally parallel to the longitudinal axis L, i.e., in the machine direction of precursor web 20, can be simply spread apart by teeth 110 and remain substantially in the first region 2 of precursor web 20.

In FIG. 2, the apparatus 100 is shown in one configuration having one patterned roll, e.g., roll 104, and one non-patterned grooved roll 102. However, in certain embodiments it may be preferable to form nip 116 by use of two patterned rolls having either the same or differing patterns, in the same or different corresponding regions of the respective rolls. Such an apparatus can produce webs with tufts 6 protruding from both sides of the tufted web 21, as well as macro-patterns embossed into the web 21.

The number, spacing, and size of tufts 6 can be varied by changing the number, spacing, and size of teeth 110 and making corresponding dimensional changes as necessary to roll 104 and/or roll 102. This variation, together with the variation possible in precursor webs 20 and the variation in processing, such as line speeds, permits many varied tufted webs 21 to be made for many purposes. For example, tufted web 21 made from a high basis weight hydrophobic fabric having MD and CD extensible threads could be made into a breathable web 1 as further discussed below for use as a breathable yet water repellent covering for hay to improvement of the forage quality of hay (for cattle feed). A tufted web 21 made from a relatively low basis weight nonwoven web of extensible spunbond polymer fibers could be used as a dusting cloth fabric for use in the home, such as to clean furniture, floors or doorknobs. As described more fully below, tufted web 21 and web 1 can also be used in disposable absorbent articles such as bandages, wraps, incontinence devices, diapers, sanitary napkins, pantiliners, and hemorrhoid treatment pads.

In some embodiments, due to the preferred method of forming tufts 6, as described below, another characteristic of tufts 6 is their generally open structure characterized by open void area 10 defined interiorly of tufts 6. By "void area" is not meant completely free of any fibers, but is meant as a general description of its general appearance. Therefore, it may be that in some tufts 6 a loose fiber 8 or a plurality of loose fibers 8 may be present in the void area 10. By "open" void area is meant that the two longitudinal ends of tuft 6 are generally open and free of fibers, such that tuft 6 forms something like a "tunnel" structure, as shown in FIGS. 4 and 5.

Figure 3:
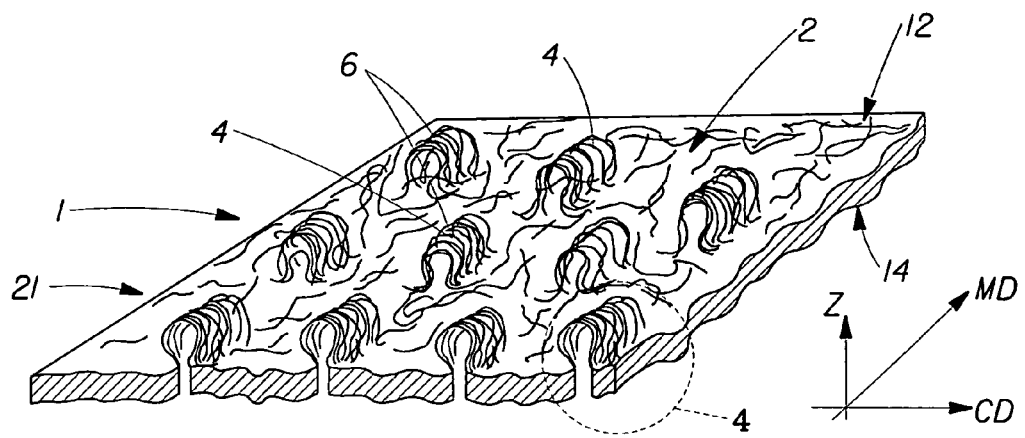
FIG. 3 is a partial perspective view of a tufted web.

Additionally, as a consequence of a preferred method of making tufted web 21, the second regions 4 associated with second surface 14 are discontinuities 16 characterized by a generally linear indentation defined by formerly random fibers of the second surface 14 having been urged directionally (i.e., the "Z-direction" as is commonly understood in the nonwoven art to indicate an "out-of-plane" direction generally orthogonal to the MD-CD plane as shown in FIGS. 3-5) into tuft 6 by the teeth of the forming structure, described in detail below. The abrupt change of orientation exhibited by the previously randomly-oriented fibers of precursor web 20 defines the discontinuity 16, which exhibits a linearity such that it can be described as having a longitudinal axis generally parallel to longitudinal axis L of the tuft 6. Due to the nature of many nonwoven webs useful as precursor webs 20, discontinuity 16 may not be as distinctly noticeable as tufts 6. For this reason, the discontinuities 16 on the second side of tufted precursor web 21 can go unnoticed and may be generally undetected unless tufted precursor web 21 is closely inspected. Thus in some embodiments, tufted precursor web 21 can have the look and feel of terry cloth on a first side, and a relatively smooth, soft look and feel on a second side. In other embodiments, discontinuities 16 can appear as apertures, and may be apertures through tufted precursor web 21 via the ends of the tunnel-like looped tufts 6.

Further, as a consequence of a preferred method of making precursor web 21, whether or not the second regions 4 have looped aligned fibers 8, each exhibits a pronounced linearity at or near the first and second surfaces 12, and 14, respectively, of precursor web 21. One can appreciate that, due to the geometry of elongated teeth 110 of roll 104, the second regions 4 of precursor web 20 each have a linear orientation associated therewith. This linear orientation is an inevitable consequence of the method of making precursor web 21 when teeth 110 also have a linear orientation, as described herein below. One way of understanding this linear orientation is to consider the linear orientation of discontinuities 16 on the second surface 14 of precursor web 21. Likewise, if tuft 6 were removed from precursor web 21 at first surface 12, the second region 4 would appear as a linear discontinuity on the first surface 12 of precursor web 21, e.g., as if a linear slit or cut had been made at the location of tuft 6. This linear web discontinuity corresponds directionally to longitudinal axis L.

From the description of tufted web 21, it can be seen that the looped fibers 8 of tuft 6 can originate and extend from either the first surface 12 or the second surface 14 of precursor web 21. Of course the fibers 8 of tuft 6 can also extend from the interior 19 of precursor web 21. The fibers 8 of tufts 6 extend due to having been urged out of the generally two-dimensional plane of precursor web 20 (i.e., urged in the "Z-direction" as shown in FIG. 3). In general, the fibers 8 or 18 of the second regions 4 comprise fibers that are integral with and extend from the fibers of the fibrous web first regions 2.

The extension of looped fibers 8 can be accompanied by a general reduction in fiber cross sectional dimension (e.g., diameter for round fibers) due to plastic deformation of the fibers and the effects of Poisson's ratio. Therefore, portions of the fibers 8 of tufts 6 can have an average fiber diameter less than the average fiber diameter of the fibers of precursor web 20 as well as the fibers of first regions 2. It has been found that the reduction in fiber cross-sectional dimension is greatest intermediate the base 5 and the distal portion 3 of tufts 6. This is believed to be due to portions of fibers at the base 5 and distal portion 3 of tufts 6 are adjacent the tip of teeth 110 of roll 104, described more fully below, such that they are frictionally locked and immobile during processing; Thus, the intermediate portions of tufts 6 are more free to stretch, or elongate, and accordingly, are freer to experience a corresponding fiber cross sectional dimension reduction.

Figure 7:
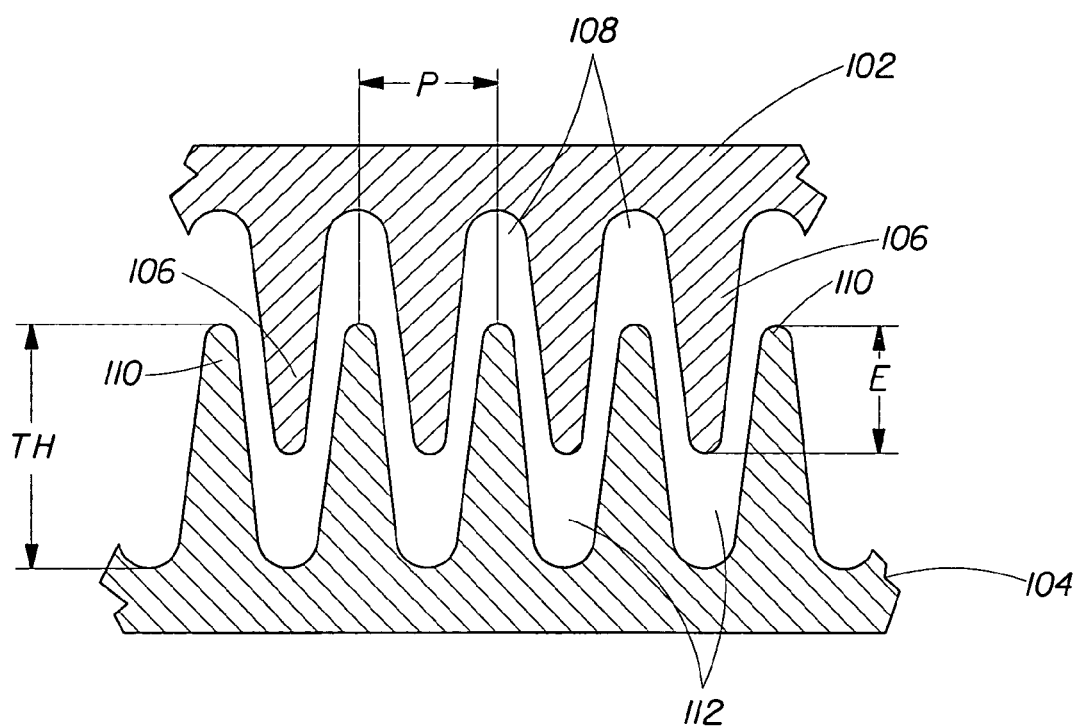
FIG. 7 is a cross-sectional depiction of a portion of the apparatus shown in FIG. 2.

FIG. 7 shows in cross section a portion of the intermeshing rolls 102 (and 102A and 102B, discussed below) and 104 including ridges 106 and teeth 110. As shown teeth 110 have a tooth height TH (note that TH can also be applied to ridge 106 height; in a preferred embodiment tooth height and ridge height are equal), and a tooth-to-tooth spacing (or ridge-to-ridge spacing) referred to as the pitch P. As shown, depth of engagement, (DOE) E is a measure of the level of intermeshing of rolls 102 and 104 and is measured from tip of ridge 106 to tip of tooth 110. The depth of engagement E, tooth height TH, and pitch P can be varied as desired depending on the properties of precursor web 20 and the desired characteristics of web 1 of the present invention. For example, in general, to obtain looped fibers in tuft 6, the greater the level of engagement E, the greater the necessary fiber mobility and/or elongation characteristics the fibers of precursor web 20 must possess. Also, the greater the density of second regions 4 desired (second regions 4 per unit area of web 1), the smaller the pitch should be, and the smaller the tooth length TL and tooth distance TD should be, as described below.

Figure 8:
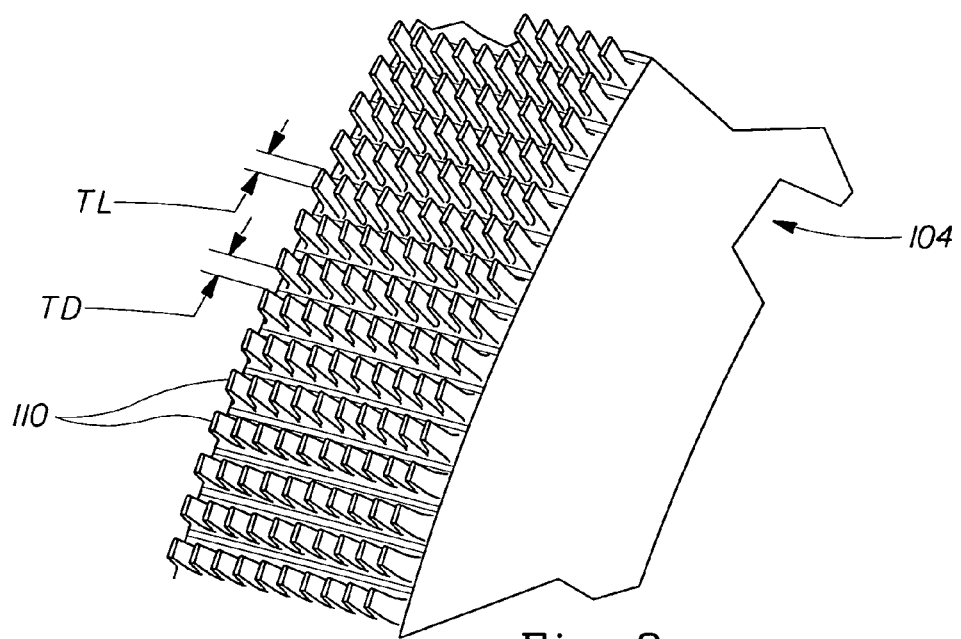
FIG. 8 is a perspective view of a portion of the apparatus for forming one embodiment the web of the present invention.
Figure 9:
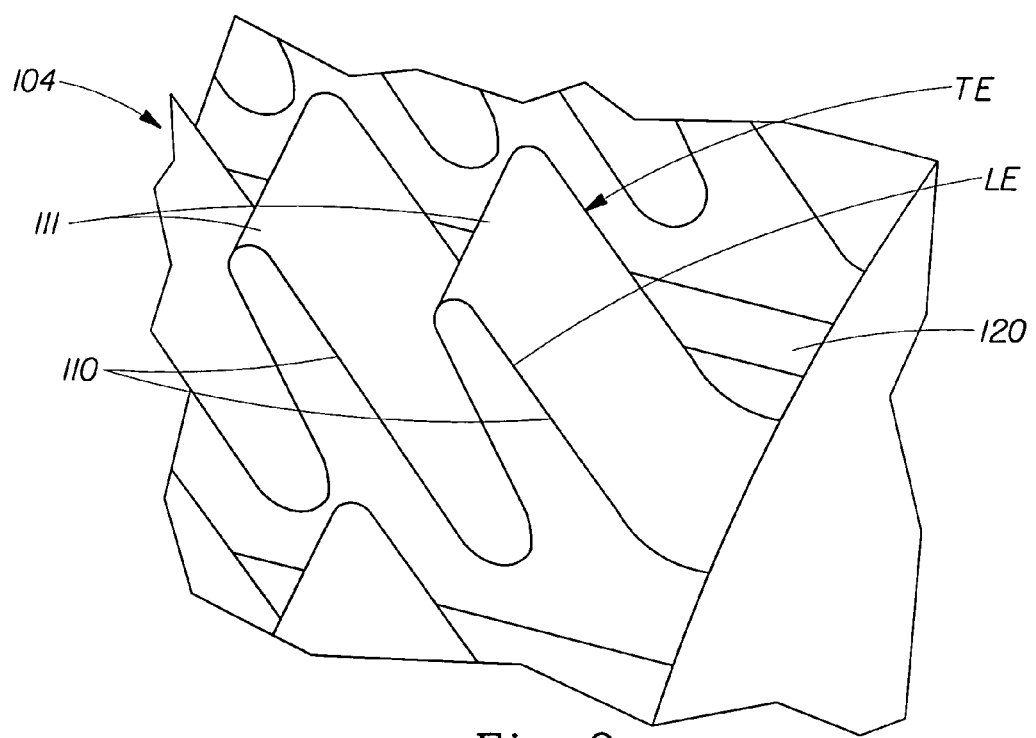
FIG. 9 is an enlarged perspective view of a portion of the apparatus for forming the web of the present invention.

FIG. 8 shows a portion of one embodiment of a roll 104 having a plurality of teeth 110 useful for making a tufted precursor web 21 or web 1 of spunbond nonwoven material from a spunbond nonwoven precursor web 20 having a basis weight of between about 60 gsm and 100 gsm, preferably about 70 gsm, or 80 gsm or 90 gsm. An enlarged view of teeth 110 shown in FIG. 8 is shown in FIG. 9. In this embodiment of roll 104, teeth 110 have a uniform circumferential length dimension TL of about 1.25 mm measured generally from the leading edge LE to the trailing edge TE at the tooth tip 111, and are uniformly spaced from one another circumferentially by a distance TD of about 1.5 mm. For making a soft, fibrous web 1 from a precursor web 20 having a basis weight in the range of about 60 to 100 gsm, teeth 110 of roll 104 can have a length TL ranging from about 0.5 mm to about 3 mm and a spacing TD from about 0.5 mm to about 3 mm, a tooth height TH ranging from about 0.5 mm to about 10 mm, and a pitch P between about 1 mm (0.040 inches) and 2.54 mm (0.100 inches). Depth of engagement E can be from about 0.5 mm to about 5 mm (up to a maximum approaching the tooth height TH). Of course, E, P, TH, TD and TL can each be varied independently of each other to achieve a desired size, spacing, and area density of tufts 6 (number of tufts 6 per unit area of web 1).

As shown in FIG. 9, each tooth 110 has a tip 111, a leading edge LE and a trailing edge TE. The tooth tip 111 can be rounded to minimize fiber breakage and is preferably elongated and has a generally longitudinal orientation, corresponding to the longitudinal axes L of second regions 4. It is believed that to get the tufts 6 of the web 1 that can be described as being tufted, the LE and TE should be very nearly orthogonal to the local peripheral surface 120 of roll 104. As well, the transition from the tip 111 and the LE or TE should be a relatively sharp angle, such as a right angle, having a sufficiently small radius of curvature such that, in use the teeth 110 push through precursor web 20 at the LE and TE. Without being bound by theory, it is believed that having relatively sharply angled tip transitions between the tip of tooth 110 and the LE and TE permits the teeth 110 to punch through precursor web 20 "cleanly", that is, locally and distinctly, so that the resulting web 1 can be described as "tufted"

in second regions 4 rather than "embossed" for example. When so processed, the web 1 is not imparted with any particular elasticity, beyond what the precursor web 20 may have possessed originally.

Although teeth 110 have been described in a preferred embodiment of being elongated, it is recognized that teeth 110 need not be elongated to produce a tufted web 1. For example, the tooth length TL can be generally equal to the tooth width, which can be varied depending upon the desired pitch P, for example. Such teeth can have an aspect ratio of tooth length to tooth width of 1:1, and can be described as having a generally square or round cross section. It is also contemplated that the size, shape, orientation and spacing of the teeth 110 can be varied about the circumference and width of roll 104 to provide for varied web 1 properties and characteristics. For example, teeth 110 can be elongated and oriented at an angle from the MD, and can even be placed such that the length dimension of tooth length TL is oriented parallel to the CD on roll 104.

Figure 10:
FIG. 10 is a photomicrograph of a portion of a web of the present invention.
Figure 11:
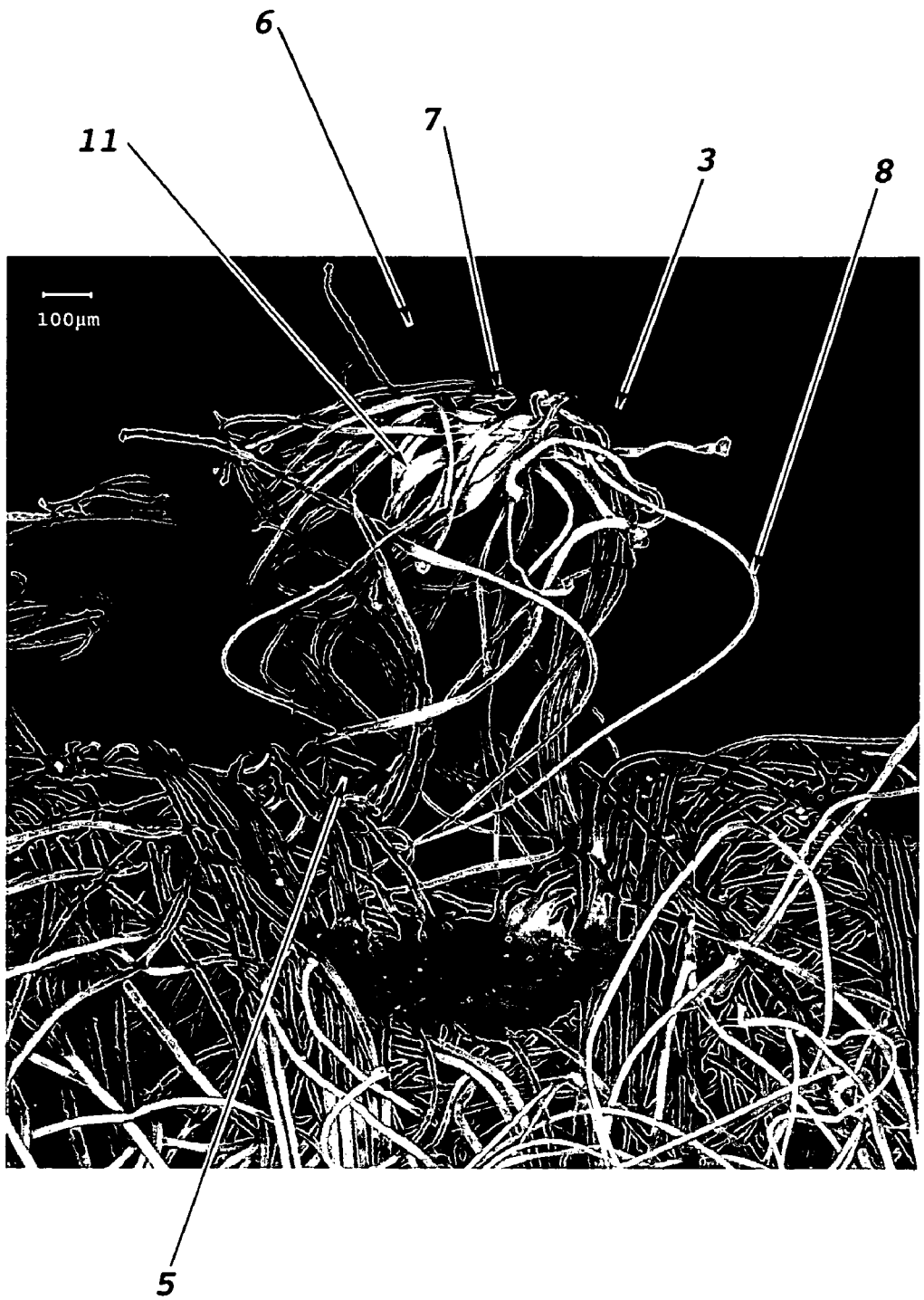
FIG. 11 is a photomicrograph of a portion of a web of the present invention.

At higher line speeds, i.e., relatively higher rates of processing through the nip of rotating rolls 102 and 104, like materials can exhibit very different structures for tufts 6, i.e., tufts. For example, FIGS. 10 and 11 show representative tufts 6 in tufted precursor webs 21 made from the same material with the same process conditions, the only difference being the rotational speed of the rolls 102 and 104, i.e., line speed (in units of length/time) of the precursor web 20 being processed into tufted precursor webs 21. The precursor web 20 used for each of the webs shown in FIGS. 10 and 11 was a 25 gsm nonwoven web comprising polypropylene and available from BBA Nonwovens, Simpsonville, S.C., and sold under the trade name Sofspan 200®. The web shown in FIG. 10 was processed through the nip 116 of rolls 102 and 104 having a depth of engagement E of about 3.4 mm (about 0.135 inch), a pitch P of about 1.5 mm (about 0.060 inch), a tooth height TH, of about 3.7 mm (about 0.145 inch), a tooth distance of TD of 1.6 mm (abut 0.063 inch), and a tooth length of TL of about 1.25 mm (about 0.050 inch). The web was run at a line speed of about 15 meters/minute (about 50 feet per minute). The web shown in FIG. 11 is identical to the web shown in FIG. 10, and was processed under identical conditions except for the line speed, which was about 150 meters per minute (about 500 feet per minute).

As can be seen from an inspection of FIGS. 10 and 11, the tufts 6 shown are noticeably different. The tuft 6 shown in FIG. 10 is similar in structure to the tufts shown in FIGS. 2-6. That is, it exhibits substantially aligned, looped fibers 8 with very few broken fibers, e.g., fibers 18 as shown in FIG. 5. The tufts 6 shown in FIG. 11, however, exhibits a very different structure, a structure that appears to be typical of some spunbond nonwoven materials processed to form tufts 6 at relatively high speeds. It is believed that such a structure is typical of highly-bonded spunbond nonwoven materials, such that the high percentage of bonded area inhibits fiber dislocation and movement during processing. This structure exhibits broken fibers between the proximal portion, i.e., base 5, of tufts 6 and the distal portion, i.e., the top 3, of tufts 6, and what appears to be a "mat" 7 of fibers at the top of the tufts 6. Mat 7 comprises and is supported at the top of tufts 6 by unbroken, looped fibers 8, and also comprises portions of broken fibers 11 that are no longer integral with precursor web 20. That is, mat 7 comprises fiber portions which were formerly integral with precursor web 20 but which are completely detached from precursor web 20 after processing at sufficiently high line speeds in the process described with reference to FIGS. 1 and 2.

Precursor webs 20 having relatively higher basis weights generally result in tufted precursor webs 21 having relatively more fiber 11 portions in mat 7. In one sense, for some precursor webs 20 it appears as if most of the fiber content of the precursor web 20 in the immediate vicinity of a tooth tip 110 during manufacture is simply displaced in the Z-direction to the distal portion 3 of tufts 6, resulting in mat 7.

Fiber-to-fiber mobility can be increased by reducing or eliminating the fiber-to-fiber bonds in precursor web 20. Thermal bonds can be completely eliminated or significantly reduced in a nonwoven intentional under-bonding in the heated calendar bonding process. This under-bonding may be achieved via lowering of the surface temperature of the heated calendar to less than optimal conditions, and/or use of lower bonding pressures. When such underbonding is performed correctly, most or all fibers are able to detach from the under-bonded site when the nonwoven is subjected to subsequent mechanical strain without significant breakage of fibers. This underbonding increases fiber-to-fiber mobility and permits greater nonwoven extensibility without premature rupture of fibers. Similarly, a hydroentangled web can be preferably less entangled to increase fiber-to-fiber mobility. For any precursor web 20, lubricating it prior to processing as disclosed herein can also increase fiber-to-fiber mobility by the reduction of coefficient of friction. For example, a mineral oil lubricant can be applied to precursor web 20 prior to it entering the nip 116 of rolls 102 and 104. Other suitable lubricants or topical treatments applied to the precursor web 20 to increase fiber-to-fiber mobility include, but are not limited to, water, surfactants, silicone containing materials, fiber finishes, fluoropolymers, and combinations thereof. Another way of increasing the fiber-to-fiber mobility is to add a melt additive to the polymer. Suitable melt additives include, but are not limited to, silicones, zinc stearate, magnesium stearate, fatty acid amides, fluoropolymers, polyethylene waxes, mineral fillers, polyethylene glycol oleiyl ethers, and other additives known to modify the coefficient of friction.

Referring back to FIG. 1, after tufts 6 are formed, tufted precursor web 21 travels on rotating roll 104 to nip 117 between roll 104 and a first bonding roll 156. Bonding roll 156 can facilitate a number of bonding techniques. For example, bonding roll 156 can be a heated steel roller for imparting thermal energy in nip 117, thereby melt-bonding adjacent fibers of tufted web 21 at the distal ends (tips) of tufts 6. Bonding roll 156 can also facilitate thermal bonding by means of pressure only, or use of heat and pressure. In one embodiment, for example, nip 117 can be set at a width sufficient to compress the distal ends of tufts 6, which at high rates of processing can cause thermal energy transfer to the fibers, which can then reflow and bond.

Bonding roll 156 can also be part of a system for applying and/or curing a bonding agent, such as an adhesive or a latex binder, to the distal ends of tufts 6. For example, bonding roll 156 can be part of a gravure printing system that prints on such a bonding agent. Depending on the type of bonding being facilitated, bonding roll 156 can be a smooth, steel surface, or a relatively soft, flexible surface. In a preferred embodiment, as discussed in the context of a preferred web below, bonding roll 156 is a heated roll designed to impart sufficient thermal energy to tufted web 21 so as to thermally bond adjacent fibers of the distal ends of tufts 6. Thermal bonding can be by melt-bonding adjacent fibers directly, or by melting an intermediate thermoplastic agent, such as polyethylene powder, which in turn, adheres adjacent fibers. Polyethylene powder can be added to precursor web 20 for such purposes.

First bonding roll 156 can be heated sufficiently to melt or partially melt fibers 8 or 18 at the distal ends 3 of tufts 6. The amount of heat or heat capacity necessary in first bonding roll 156 depends on the melt properties of the fibers of tufts 6 and the speed of rotation of roll 104. The amount of heat necessary in first bonding roll 156 also depends on the pressure induced between first bonding roll 156 and tips of teeth 110 on roll 104, as well as the degree of melting desired at distal ends 3 of tufts 6. In one embodiment, bonding roll 156 can provide sufficient heat and pressure to not only melt bond fibers at the distal ends 3 of tufts 6, but also cut through the bonded portion so as to, in effect, cut through the end of tuft 6. In such an embodiment, the tuft is divided into two portions, but is not longer looped. In one embodiment, pressure alone can cause the looped portion of the tuft to be cut through, thereby rendering the tufts 6 to be un-looped tufts of fiber free ends. Other methods known in the art, such as use of a spinning wire brush wheel can also be utilized to cut the loops of looped fibers to form un-looped tufts.

In one embodiment, first bonding roll 156 is a heated steel cylindrical roll, heated to have a surface temperature sufficient to melt-bond adjacent fibers of tufts 6. First bonding roll can be heated by internal electrical resistance heaters, by hot oil, or by any other means known in the art for making heated rolls. First bonding roll 156 can be driven by suitable motors and linkages as known in the art. Likewise, first bonding roll can be mounted on an adjustable support such that nip 117 can be accurately adjusted and set.

In one embodiment, bonding via bonding roll 156 can be combined with application of lotion, pressure sensitive adhesive, ink, paint, or other coatings as desired. For example, heated bonding roll 156 can be a gravure roll that can apply sufficiently high-temperature inks to impart a printed design on tufted precursor web 21. Likewise, a lotion suitable for providing a skin benefit can be applied by bonding roll 156. A key advantage of applying ink or other coatings in this manner is that the coating can be deposited on the distal ends of tufts 6, thereby conserving the amount of coating necessary to effectively coat one side of web 1. In another embodiment, application of lotions, coatings, inks, and the like, can be added without bonding via bonding roll 156.

Figure 12:
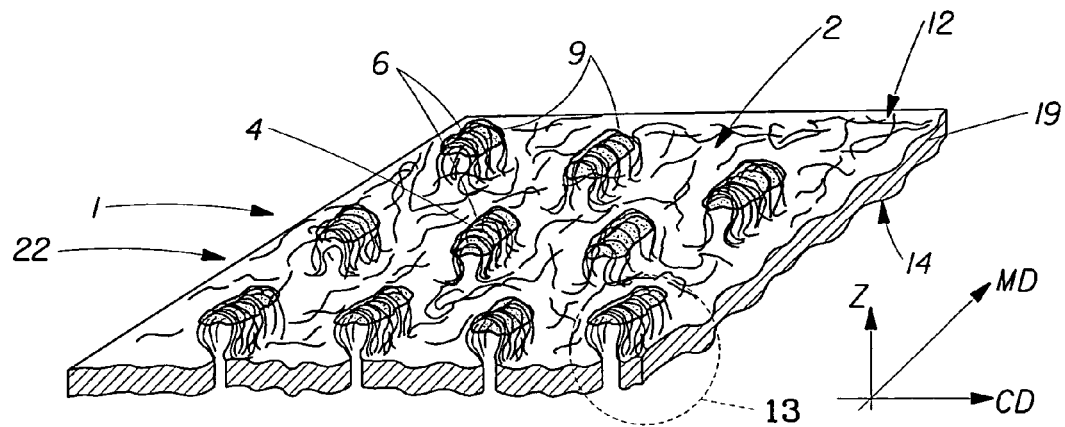
FIG. 12 is a partial perspective view of a tufted web having melt-bonded portions of tufts.
Figure 13:
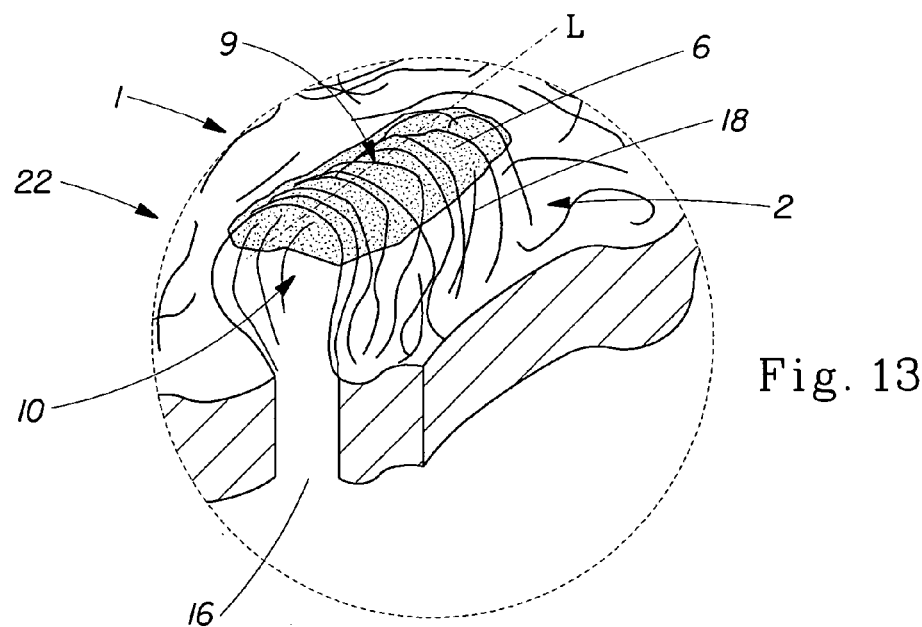
FIG. 13 is an enlarged portion of the web shown in FIG. 12.

FIG. 12 shows a portion of tufted precursor web 21 after being processed through nip 117 to be intermediate web 22, which, without further processing can be a web 1 of the present invention. Intermediate web 22 is similar to tufted precursor web 21 as described earlier, except that the distal ends 3 of tufts 6 are bonded, and are preferably thermally melt-bonded such that adjacent fibers are at least partially bonded to form distally-disposed melt-bonded portions 9. In one embodiment, intermediate web 22 can be made from a precursor web 20 comprising 80 gsm spunbond nonwoven comprising 100% polyethylene/polypropylene (sheath/core) bicomponent fibers. After forming tufts 6 by the process described above, the distal portions 3 of tufts 6 can be heated to thermally join the polyethylene portions of discrete bicomponent fibers such that adjacent fiber portions are joined to one another to form tufts 6 having melt-bonded portions 9.

The distally-disposed melt-bonded portions 9 can be made by application of thermal energy and pressure to the distal portions of tufts 6. The size and mass of the distally-disposed melt-bonded portions 9 can be modified by modifying the amount of heat energy imparted to the distal portions of tufts 6, the line speed of apparatus 150, and the method of heat application.

In another embodiment, distally-disposed melt-bonded portions 9 can be made by application of radiant heat. That is, in one embodiment bonding roll 156 can be replaced or supplemented by a radiant heat source, such that radiant heat can be directed toward tufted precursor web 21 at a sufficient distance and corresponding sufficient time to cause fiber portions in the distally-disposed portions of tufts 6 to soften or melt. Radiant heat can be applied by any of known radiant heaters. In one embodiment, radiant heat can be provided by a resistance-heated wire disposed in relation to tufted precursor web 21 such that it is extended in the CD direction at a sufficiently-close, uniformly-spaced distance that as the web is moved in relation to the wire, radiant heat energy at least partially melts the distally-disposed portions of tufts 6. In another embodiment, a heated flat iron, such as a hand-held iron for ironing clothes, can be held adjacent the distal ends 3 of tufts 6, such that melting is effected by the iron.

The benefit of processing the intermediate web 22 as described above is that the distal ends 3 of tufts 6 can be melted under a certain amount of pressure in nip 117 without compressing or flattening tufts 6. As such, a three-dimensional web can be produced and set, or "locked in" to shape, so to speak by providing for thermal bonding after forming. Therefore, a substantially unbonded web can be processed by the apparatus 150 to be bonded and formed in a manner that helps ensure the web maintains its three-dimensionality. Such a set three-dimensional web can have desirable stretch or elastic properties, depending upon the type of web material used and the amount of set induced. Moreover, the distally-disposed bonded or melt-bonded portions 9 can aid in maintaining the tufted, lofty structure of tufts 6 when web 1 is subjected to compression or shearing forces. For example, a web 1 processed as disclosed above to have tufts 6 comprising fibers integral with but extending from first region 2 and having distally-disposed melt-bonded portions 9 can have improved shape retention after compression due to winding onto a supply roll and subsequently unwinding. It is believed that by bonding together adjacent fibers at distal portions of tufts 6, the tufts experience less random collapse upon compression; that is, the entire structure of tufts 6 tends to move together, thereby permitting better shape retention upon a disordering event such as compression and/or shear forces associated with rubbing the surface of the web. When used in a wiping or rubbing application, the bonded distal ends of tufts 6 can also reduce or eliminate fuzzing or pilling of web 1.

In another embodiment web 1 can have melt-bonded portions that are not, or not only, at distally-disposed portions of tufts 6. For example, by using a mating ridged roller instead of a flat, cylindrical roll for bonding roll 156 other portions of the tuft 6 such as at locations intermediate the base 5 and distal end 3. Likewise, continuous lines of melt-bonded material could be made on first surface 12 between rows of tufts 6.

In general, while one first bonding roll 156 is illustrated, there may be more than one bonding roll at this stage of the process, such that bonding takes place in a series of nips 117 and/or involving different types of bonding rolls 156. Further, rather than being only a bonding roll, similar rolls can be provided to transfer various substances to precursor web 20 or tufted web 21, such as various surface treatments to impart functional benefits. For example, first side 12 of tufted web 21 or intermediate web 22 can be printed with ink to impart various designs or indicia. Rolls similar to bonding roll 156 can be, for example, gravure printing rolls. Additionally, skin care lotions, surfactants, hydrophobic substances, and the like can be imparted to first side 12 of tufted web 21 or intermediate web 22 including the distal ends 3 of tufts 6. Additional rolls for such purposes can be placed in apparatus 150 before and/or after bonding roll 156. Any processes known in the art for such application of treatments can be utilized.

Additionally, substances such as lotions, ink, surfactants, and the like can be sprayed, coated, slot coated, extruded, or otherwise applied to tufted web 21 or intermediate web 22 before or after bonding roll 156. Any processes known in the art for such application of treatments can be utilized.

Further, in one embodiment an additional web can be introduced (not shown in FIG. 1) at nip 117 and bonded onto tufted precursor web 21 in nip 117. That is, an additional web can be supplied from roll stock, for example, and brought in at nip 117 to form a laminate structure, the laminate being bonded between the distal ends 3 of tufts 6 and the additional web. In this manner, a laminate having substantially flat, smooth outer surfaces and having substantial void volume can be produced. In such an embodiment, the tufts 6 are internal and separate the two outer surfaces of the laminate. By using relatively stiff fibers in tufts 6, such a laminate can be a soft, compression resistant nonwoven composite web.

Intermediate web 22 can be taken up on a supply roll for further processing as web 1 of the present invention. However, in a preferred embodiment of web 1, intermediate web 22 is further processed by being removed from roll 104 after nip 118, as depicted in FIG. 1. Nip 118 is formed between roll 104 and 102B, with roll 102B preferably being identical to roll 102A. The purpose of going around roll 102B is to remove intermediate web 22 from roll 104 without disturbing the tufts 6 formed thereon. Because roll 102B intermeshes with roll 104 just as roll 102A did, tufts 6 can fit into the grooves 108 of roll 102B as intermediate web 22 is wrapped around roll 102B.

Intermediate web 22 can be processed through nip 119 between roll 102B and second bonding roll 158. Second bonding roll 158 can be identical in design to first bonding roll 156. Second bonding roll 158 can provide sufficient heat to at least partially melt a portion of the second surface 14 of intermediate web 22 to form a plurality of non-intersecting, substantially continuous melt-bonded regions 11 corresponding to the nip pressures between the tips of ridges 106 of roll 102B and the generally flat, smooth surface of roll 158.

Second bonding roll can be used as the only bonding step in the process (i.e., without first having intermediate web 22 formed by bonding the distal ends of tufts 6). In such a case web 1 would be a tufted web with bonded portions on the second side 14 thereof. However, in general, web 1 is preferably a double bonded web 1 having bonded distal ends of tufts 6 and a plurality of non-intersecting, substantially continuous melt-bonded regions 11 on second side 14 thereon.

In general, as with first bonding roll 156, second bonding roll 158 can facilitate bonding by chemical bonding, such as by application of adhesive or latex binder materials, or bonding by pressure alone or in combination with heat. Likewise, as with first bonding roll 156, in a preferred embodiment, second bonding roll 158 is heated roll, heated to a sufficient temperature to melt-bond adjacent fibers of intermediate web 22 as web 22 goes through nip 119 to form double bonded web 23, which can be web 1 of the present invention.

Figure 14:
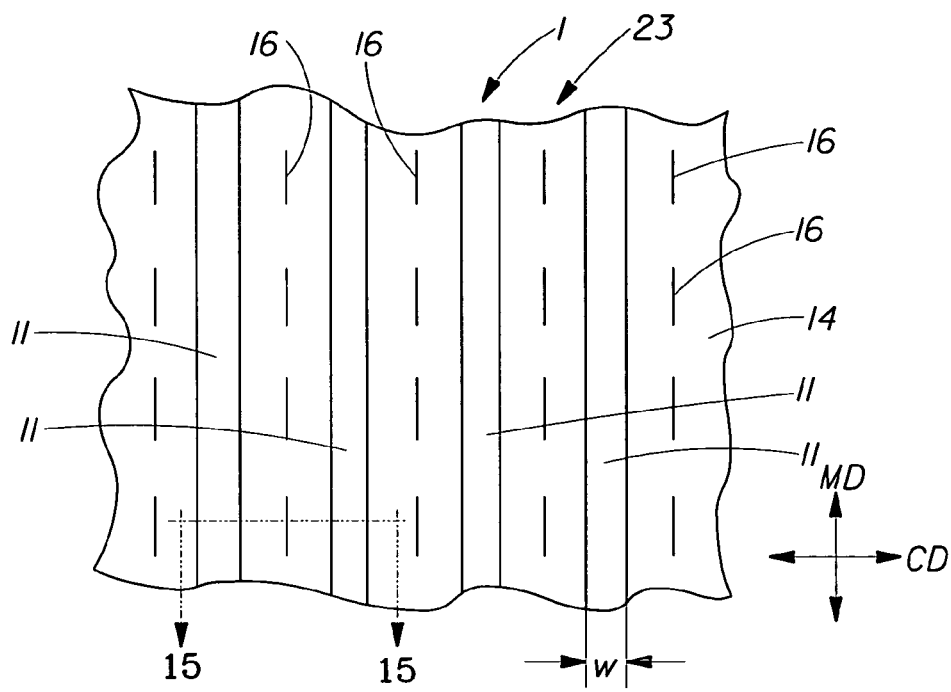
FIG. 14 is a plan view of a portion of a web of the present invention.

As shown in FIG. 14, melt-bonded regions 11 can be generally straight, parallel stripes or bands of melt-bonded material. Note that this description is for heated roll 158. For adhesive bonded embodiments, the same structure of bonded regions can be achieved, but it would not, of course, be "melt-bonded". In general, it is not necessary that a band or stripe of melt-bonded material be disposed between every row of discontinuities 16 (i.e., between every row of tufts 6). Second bonding roll 158 can be designed to only make contact in nip 119 at predetermined locations, such that the number and placement of stripes of melt-bonded material 11 can be varied as desired. Additionally, if ridges 106 of roll 104 are discontinuous, the melt-bonded portions can be discontinuous strips or bands of material that can appear, for example, as dashes or dots in the MD orientation.

There are many variations that can result based on the use of the web 1. The melt bonded regions 11 can be in rows which may form a type of perforation for tearing or may mechanically weaken the material. Alternatively, it may be desired to only have intermittent or staggered melt bonded regions 11 in some webs 1. This may be desired where strength of the material is important. The intermittent or staggered melt bonded regions 11 can result from staggering the teeth 110 or through other mechanical adjustments.

Figure 15:
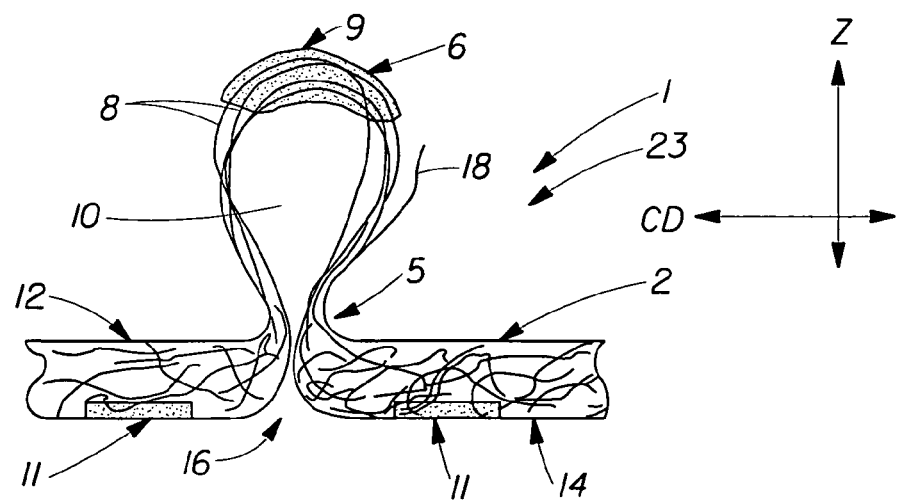
FIG. 15 is a cross-sectional view of a portion of the web shown in FIG. 14.

As shown in the cross-section of FIG. 15, web 1 of the present invention can have melt-bonded regions on the distal ends of tufts 6 as well as stripes or bands of melt-bonded regions 11 on the second surface 14. Melt-bonded regions 11 may be substantially only surface bonded, or, depending upon the time, pressure, and temperature relationship in nip 119, can be substantially bonded throughout web 1 to even bond some fibers on first surface 12. As with first bonding roll 156, the heat output of second bonding roll 158 can be adjusted to provide the amount of thermal heat transfer necessary to produce the amount of melt-bonding desired in regions 11.

In general, while one second bonding roll 158 is illustrated in FIG. 1, there may be more than one bonding roll at this stage of the process, such that bonding takes place in a series of nips 119 and/or involving different types of bonding rolls 158. In such a case, it may be that the circumference of rolls 102B and 158 be adjusted accordingly such that multiple rolls 158 can form nips 119 around circumference of roll 102B. Further, rather than being only a bonding roll, similar rolls can be provided to transfer various substances to web 1, such as various surface treatments to impart functional benefits. For example, first side 12 of tufted web 21 or intermediate web 22 can be printed with ink to impart various designs or indicia. Rolls similar to bonding roll 156 can be, for example, gravure printing rolls. Additionally, skin care lotions, surfactants, hydrophobic substances, and the like can be imparted to first side 12 of tufted web 21 or intermediate web 22 including the distal ends 3 of tufts 6. Additional rolls for such purposes can be placed in apparatus 150 before and/or after bonding roll 156. Any processes known in the art for such application of treatments can be utilized.

Additionally, substances such as lotions, ink, surfactants, and the like can be sprayed, coated, slot coated, extruded, or otherwise applied to tufted web 21 or intermediate web 22 before or after bonding roll 156. Any processes known in the art for such application of treatments can be utilized.

In some embodiments, it may be desired to form apertures at the melt-bonded regions. The melt-bonded regions on the distal ends of tufts 6 and the melt-bonded regions 11 on the second surface 14 may be opened or formed into an aperture by utilizing a stretching step after the melt-bonded regions are formed. The stretching step can be ring rolling or any other type of stretching. If apertures are desired at the base of a loop, melt-bonded regions 11 on the second surface 14 can be formed and then the web 11 ring rolled.

After web 1 is formed, it can be taken up on a supply roll 160 for storage and further processing as a component in other products.

Webs 1 of the present invention offer many opportunities for producing engineered materials having selected characteristics. For example, a web 1 can be made by selecting the length of staple fibers in a carded precursor web 20 so that the probability of having fiber ends exposed in tufts 6 can be statistically predicted. Also, a carded web of staple fibers can be blended or laminated with a spunbond nonwoven web to produce a hybrid, such that the tufts 6 comprise primarily looped spunbond fibers and the first regions 2 comprise both carded and spunbond fibers. The type of fibers, the length of staple fibers, the layering of fibers, and other variations of precursor web 20 can be varied as desired to produce desired functional characteristics of the web 1.

One of the advantages of the process and apparatus of the present invention is the production of bonded nonwoven webs from precursor web (or webs) 20 in which there are minimal fiber-to-fiber bonds. For example, the precursor web can be a nonwoven web having a pattern of discrete thermal point bonds, as is commonly known in the art for nonwoven webs. In general, however, it is desirable to minimize the number and maximize the spacing of bond points so as to allow for maximum fiber mobility and dislocation. Alternately, an unbonded precursor web 20 can be utilized, provided proper care and technique is used to present the unbonded web to the nip 116. Proper care and technique can be achieved, for example, by use of a vacuum conveyor belt from fiber laydown to nip 116. In such a web fibers can have maximum fiber mobility, and web bonding can occur at first bonding roller 156 to form a stabilized, tufted web. In general, utilizing fibers having relatively high diameters, and/or relatively high extension to break, and/or relatively high fiber mobility, results in better and more distinctly formed tufts 6.

Although web 1 is disclosed in preferred embodiments as a single layer web made from a single layer precursor web 20, it is not necessary that it be so. For example, a laminate or composite precursor web 20 having two or more layers or plies can be used. In general, the above description for web 1 holds, recognizing that looped aligned fibers 8, for example, formed from a laminate precursor web could be comprised of fibers from one, or both (or all) layers of the laminate. In such a web structure, it can be important, therefore, that fibers of all the layers have sufficient diameter, elongation characteristics, and fiber mobility, so as not to break prior to extension and tuft if it is desirable that fibers from all the layers of the laminate contribute to the tufts 6.

Multilayer webs 1 can have significant advantages over single layer webs 1. For example, a tuft 6 from a multilayer web 1 using two precursor webs 20A and 20B, can comprise fibers in a "nested" relationship that "locks" the two precursor webs together, forming a laminate web without the use or need of adhesives or thermal bonding between the layers. In other embodiments, multilayer webs can be chosen such that the fibers in the layers do not have equal extensibility. Such webs can produce tufts 6 by pushing fibers from a lower layer up and through an upper layer which contributes few or no fibers to tuft 6. For example, the upper layer of a laminate web could be a polymer film which is simply "poked through" when processed by the apparatus of the present invention. In such a web, second bonding roll 158 may be utilized to melt-bond the polymer film to an upper nonwoven layer, for example. In general, additional layers of material, including additional web layers can be joined, such as by bonding, to web 1 by laminating to either side of web 1.

In a multilayer web 1 each precursor web can have different material properties, thereby providing web 1 with beneficial properties. For example, web 1 comprising two (or more) precursor webs, e.g., first and second precursor webs 20A and 20B can have beneficial fluid handling properties for use as a topsheet on a disposable absorbent article, as described more fully below. For superior fluid handling, for example, first precursor web 20A can form an upper layer (i.e., a body-contacting when used as a topsheet on a disposable absorbent article) and be comprised of relatively hydrophobic fibers. Second precursor web 20B can form a lower layer (i.e., disposed between the topsheet and an absorbent core when used on a disposable absorbent article) comprised of relatively hydrophilic fibers. Fluid deposited upon the upper, relatively hydrophobic layer is quickly transported to the lower, relatively hydrophilic, layer. One reason for the observed rapid fluid transport is the capillary structures formed by the generally aligned fibers 8, 18 of tufts 6. The fibers 8, 18 form directionally-aligned capillaries between adjacent fibers, and the capillary action is enhanced by the general convergence of fibers near proximal portion 5 of tufts 6.

It is believed that the rapid fluid transport is further increased due to the ability of fluid to enter the web 1 via the voids 10 created by tufts 6. This "lateral entry" capability and/or capillary action, and/or the hydrophilicity gradient afforded by the structure of web 1 makes web 1 an ideal material for optimal fluid handling for disposable absorbent articles. In particular, a multilayer web 1 can provide for even greater improvement in fluid handling characteristics. When web 1 is used as a fluid handling member in a disposable absorbent product, web 1 can be oriented so that first surface 12 is oriented facing toward the body of the wearer or away from the body of the wearer. Thus, in one embodiment the tufts would be extending toward the skin of the wearer, and in the other embodiment the tufts would extend away from the wearer and toward other components of the disposable absorbent article, or a garment of the wearer.

In another embodiment, first precursor web 20A can be comprised of relatively soft fibers (e.g., polyethylene), while second precursor web 20B can be comprised of relatively stiff fibers (e.g., polyester). In such a multilayer web 1, tufts 6 can retain or recover a certain amount of height h as depicted in FIG. 15, even after applied pressure. The benefit of such as structure, particularly when combined with a hydrophilicity gradient as described above (fibers can be rendered hydrophobic or hydrophilic by means known in the art), is a web 1 suitable for use as a topsheet in feminine hygiene products that provides for superior fluid acquisition and superior rewet properties (i.e., reduced fluid movement back to the surface of the topsheet). It is believed that the increased stiffness provided by the relatively stiff fibers of second precursor web 20B provide for increased compression resistant caliper (thickness) of the web, while the relatively soft fibers of first precursor web 20A provides for softness at the web/skin interface. This extra caliper, together with the ability of the distally-disposed portions 3 of tufts 6 to remain relatively fluid free (due to lack of capillarity because adjacent fibers bonded together), results in a superior, soft, dry (and dry-feeling) topsheet for use in feminine hygiene products, as well as baby diapers, adult incontinence articles, bandages, and the like.

Figure 16:
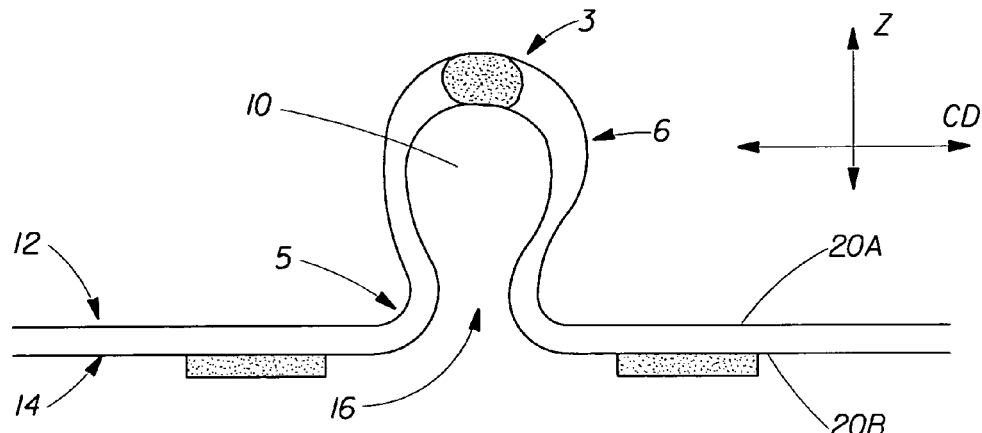
FIGS. 16-18 are schematic representations of cross-sections of tufts of multi-layer webs of the present invention.
Figure 17:
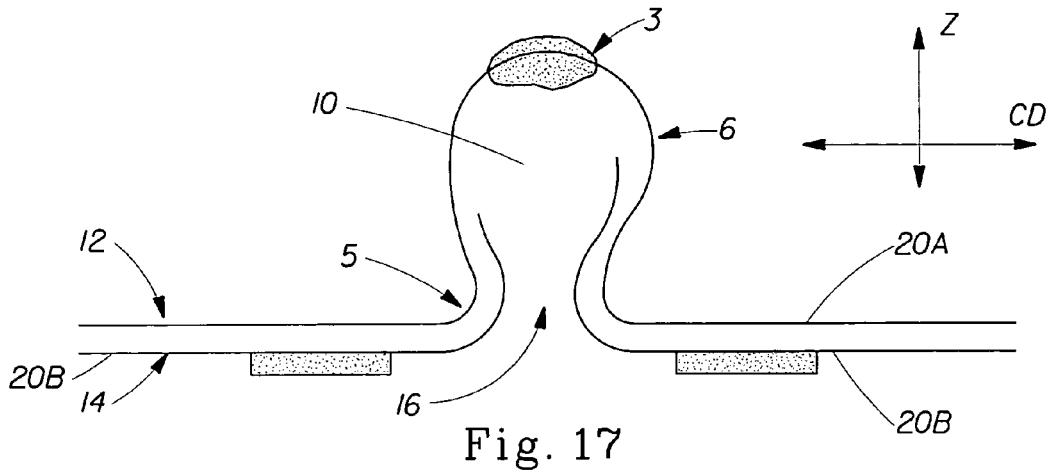
Figure 18:
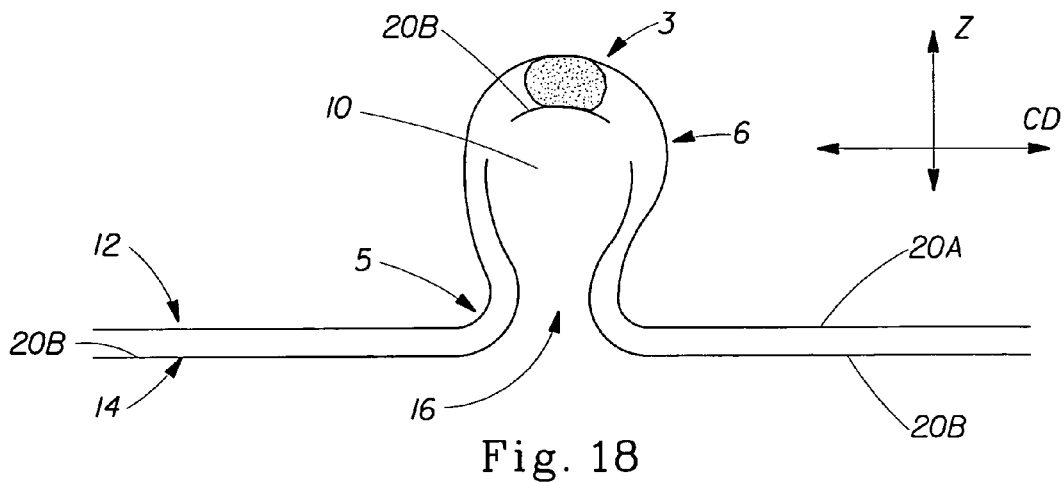

FIGS. 16-18 show representative schematic diagrams of possible structures for tufts 6, depending on the material properties of precursor webs 20A or 20B. Other structures, not shown, can be achieved, with the only limitation to various structures being the limitations inherent in the material properties of the precursor webs.

Therefore, as can be seen from the above description, depending on the precursor web 20 (or webs) utilized and the dimensional parameters of rolls 102 and 104, including teeth 110, and heating properties of first and/or second bonding rolls 156 and 158, web 1 of the present invention can exhibit a wide range of physical properties. The web 1 can exhibit a range of texture subjectively experienced as ranging from softness to roughness, an absorbency ranging from non-absorbent to very absorbent, a bulkiness ranging from relatively low bulk to relatively high bulk; a tear strength ranging from low tear strength to high tear strength; an elasticity ranging from non-elastic to at least 100% elastically extensible, a chemical resistance ranging from relatively low resistance to high resistance, depending on the chemical considered, and many other variable parameters generally described as shielding performance, alkali resistance, opacity, wiping performance, water absorptivity, oil absorptivity, moisture permeability, heat insulating properties, weatherability, high strength, high tear force, abrasion resistance, electrostatic controllability, drape, dye-affinity, safety and the like. In general, depending on the elongation properties of the fibers of precursor web 20, the dimensions of apparatus 150 can be varied to produce a web 1 having a wide range of dimensions associated with second regions 4, including the height h (as shown in FIG. 15), and spacing, including the area density of discrete tufts 6.

In one embodiment, a two-layer laminate web 1 can be produced by the method and apparatus disclosed herein having a heated roll temperature of 275 degrees F. (135 degrees C.) for first and second heated rolls 156 and 158. The depth of engagement E in nip 116 can be from about 0.070 inches (about 1.8 mm) to about 0.100 inches (2.54 mm) and can be about 0.130 inches (about 3.4 mm). The tooth height TH can be from about 0.070 inches (about 1.8 mm) to about 0.130 inches (about 3.4 mm and the pitch P can be from about 0.060 inches (about 1.5 mm) to about 0.130 inches (about 3.4 mm). The laminate web can be run at a line speed of from about 50 feet per minute (about 15 meters per minute) to about 500 feet per minute (about 150 meters per minute).

In multilayer embodiments, one layer can be a 45 gsm 50%/50% 6 denier PET/bicomponent thermal point bonded carded web. The PET fibers can be surfactant treated PET, crimped, 2-inch (50 cm) cut length fibers having a round cross-sectional shape, obtained from Wellman, Inc., Charlotte, N.C. under the designation Type 204. The bicomponent fibers can be relatively hydrophilic 6 denier polyethylene/polypropylene crimped, 2-inch cut length bicomponent binder fibers (higher melting polypropylene core/low melting point polyethylene sheath) obtained from Fibervision LB, Atlanta Ga., under the designation Type T425. All percentages refer to weight percent.

Another two-layer embodiment of web 1 can be made like the one described above, but having a heated roll temperature of 295 degrees F. (146 degrees C.) for first and second heated rolls 156 and 158 and a line speed of 500 feet per minute (about 152 meters per minute).

Both of the two layer embodiments of web 1 described above utilize nonwoven precursor webs having differences at least in their relative hydrophilicity and are suitable for use in a catamenial products, particularly as a cover sheet (e.g., topsheet) for sanitary napkins, as described more fully below. In another embodiment, first precursor web can be a nonwoven and second precursor web a polymer film, such that when tufts 6 are formed, the polymer film forms a cover, or cap over the tuft. For example, in the embodiment shown schematically in FIG. 16, precursor web 20A can be a polymer film, which can be seen to form a cover over the tufted portion of precursor web 20B.

In another embodiment, one of the precursor webs can be a paper web, such as a tissue paper web similar to BOUNTY® paper towels sold by The Procter & Gamble Co. In one embodiment, a meltblown or spunbond nonwoven web can be laminated to the paper web and processed by apparatus 150 to form a paper/nonwoven composite laminate. The nonwoven web can be pre-heated, or deposited directly onto paper web while in a heated condition. In one embodiment, spunbond or meltblown layer of polymeric fibers having a basis weight of between about 3 to about 20 grams per square meter can be applied from one or more beams of an SMS line directly onto a moving web of tissue paper to form a tissue/nonwoven laminate. The tissue/nonwoven laminate can be further laminated with another tissue layer to form a tissue/nonwoven (e.g., meltblown)/tissue and then processed through the nip 116 of apparatus 150. Even without subsequent heating of the web as disclosed above, the resulting tufted web has been found to have excellent integrity for wiping applications, for example.

In another embodiment, a paper web can be utilized as precursor web 20 in which the paper web comprises thermoplastic fibers. For example, thermoplastic fibers can be added in the pulp furnish during the wet stage of papermaking in a sufficient amount to permit thermal bonding of the thermoplastic fibers to give increased integrity to the tufted web 1. For example, a sufficient amount can be from about 10 to about 20% polymer fibers by weight of cellulosic fibers in a papermaking furnish.

Figure 19:
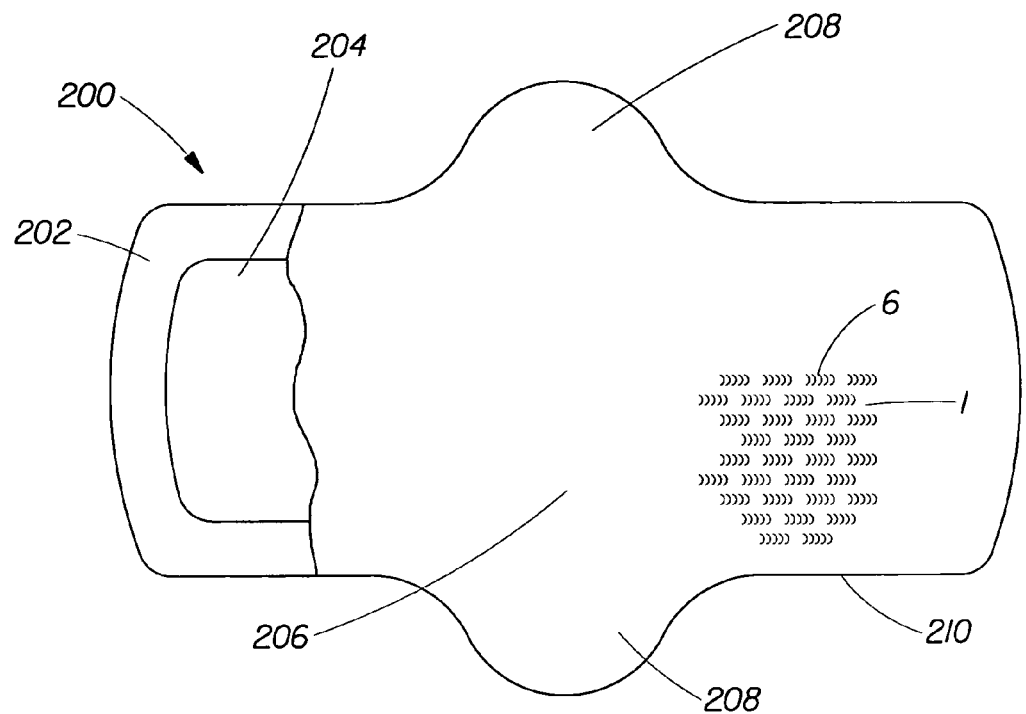
FIG. 19 is a partial cut away plan view of a sanitary napkin of the present invention.

FIG. 19 shows in partial cut away plan view a catamenial article, specifically a sanitary napkin, having as one of its components a web 1 of the present invention. In general, sanitary napkin 200 comprises a backsheet 202, a topsheet 206 and an absorbent core 204 disposed between the topsheet 206 and backsheet 202 which can be joined about the periphery 210. Sanitary napkin 200 can have side extensions, commonly referred to as "wings" 208 designed to wrap the sides of the crotch region of the panties of the user of sanitary napkin 200. Topsheet 206 of sanitary napkin 200 comprises web 1 having tufts 6 on a body facing side thereof. Sanitary napkins, including topsheets for use as the body facing surface thereof, are well known in the art and need no detailed description of various alternative and optional designs. Other catamenial articles, such as panty liners, interlabial devices, will also have similar structure as sanitary napkins. It is noted that web 1 can be used as, or as a component of, one or more of a backsheet, absorbent core material, topsheet, secondary topsheet, or wing material.

Figure 20:
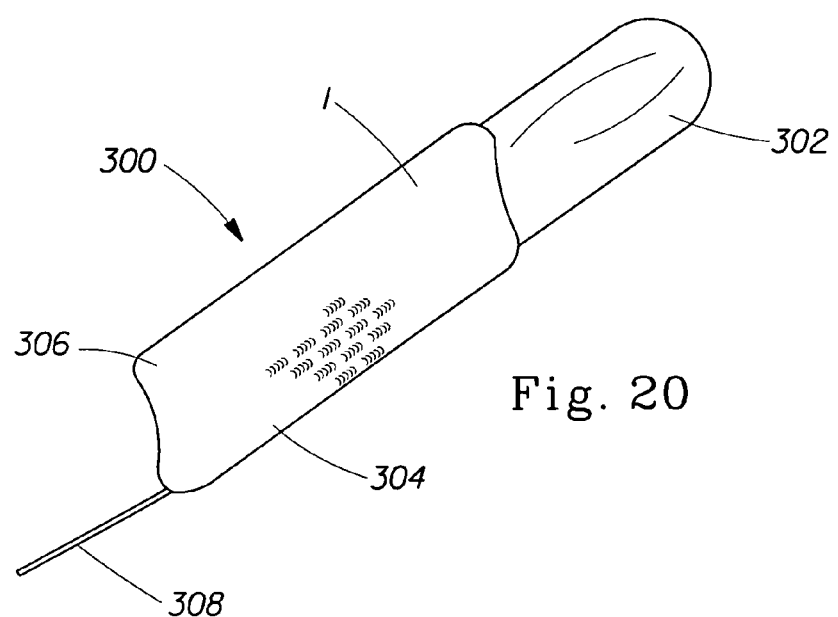
FIG. 20 is a partial cut away perspective view of a tampon of the present invention.

FIG. 20 shows in partial cut away perspective view a catamenial tampon 300 having as one of its components a web 1 of the present invention. In general, tampon 300 comprises a compressed absorbent core 302 and a fluid permeable cover wrap 304 that covers absorbent core 302. Cover wrap 304 may extend beyond one end of absorbent core 302 to form a skirt portion 306. A removal means, such as string 308 can be provided to facilitate removal of the tampon after use. Tampons, including cover wraps for use as the body contacting surface thereof, are well known in the art and need no detailed description of various alternative and optional designs. However, it is noted that web 1 can be used as, or as a component of, one or more of a cover wrap, absorbent core material, or removal means material. On other disposable absorbent articles, such as baby diapers having mechanical fasteners, web 1 can be one of the components of a hook and loop fastener, for example. Web 1 can be either the landing zone of such a fastener, or the hook portion of a tape tab designed to engage such a landing zone.

The web of the present invention can also be utilized in wiping articles, such as textured body cloths for cleansing and moisturizing the body. In one embodiment, a web 1 can be incorporated into a dual textured lathering article for cleansing the body in a shower. The wipe 1 can include a lathering surfactant component which is prepared from the ingredients shown in Table 1 below.

TABLE 1

Surfactant ingredients

| Ingredient | Supplier or common CTFA name | Amount added |
|---|---|---|
| Alkyl Glyceryl Sulfonate (AGS) 47.5% solids paste | (Procter & Gamble Co., Iowa City, Iowa, USA) | 62.8% |
| Lauramidopropyl Betaine, 30-35% active | Colonial Chemical Inc., USA | 19.7% |
| Citric Acid Anhydrous | Citric acid | 0.2% |
| Propylene Glycol | Propylene glycol | 15.2% |
| Polyox WSR-301 | (Amerchol) PEG 90M | 0.20% |
| JR30M | (Amerchol) Polyquaternium-10 | 0.50% |
| Perfume | | 1.0% |
| Preservative & misc. | | 0.4% |

The ingredients can be prepared by mixing the cationic polymer with the glycol and surfactants under heat with continuous stirring to avoid lumps. The perfume can be added during cooling. The lathering surfactant component melts upon heating to about 60 degrees C. or more, and solidifies upon cooling to a hard solid. The percentages are weight percentages of the ingredient including water it may contain.

The ingredients above can be applied to a layered, laminated web 1 prepared by the process described above with respect to the apparatus of FIG. 1. Web 1 can be a 25 gsm nonwoven web comprising polypropylene and available from BBA Nonwovens, Simpsonville, S.C., and sold under the trade name Sofspan 200®, processed by the apparatus of the invention to have melt-bonded regions on the distal ends of tufts 6 as well as stripes or bands of melt-bonded regions 11 on the second surface 14. The web 1 so prepared is sealed to a batting, which is a lofty, airlaid blend of carded fibers (50% PET, 50% PE/PP core-sheath bicomponent) having a basis weight of 65 gsm and a thickness of 2.7 mm, from Libeltex Nev., Belgium. The nonwoven web gives a textured feel and increased stability during use to the article. The lathering surfactant component can be heated until liquid, and slot coated in 3 rows between the nonwoven and airlaid layers at a rate of 4 grams per finished article. The layers can be sealed using an ultrasonic sealer such as a Branson Model 9000 Ultrasonic Sealer, which seals a dot pattern comprising a grid of 4 mm diameter sealing points spaced evenly across the article at 3 cm intervals. The sealed web can be cut into 11.9 cm×9.0 cm rectangles to create the finished article.

A second example of a layered laminated article using a web 1 of the present invention can incorporate a commercial body wash which has about 16% active surfactants. The body wash is commercially available and distributed by Bath & Body Works and comprises water, sodium laureth sulfate, lauramide DEA, TEA cocoyl glutamate, cocamidopropyl betaine, fragrance, sodium PCA, aloe leaf juice, carica papaya fruit extract, propylene glycol, polyquaternium-10, preservatives, fragrance, PEG-150 distearate, sodium chloride and colors. A layered nonwoven/airlaid web can be prepared as in the example above, and then soaked in the commercial body wash described above, which is preferably added to the web at the rate of 1100 gsm. The webs can be dried in a forced air oven, turning them over when partially dry and wiping excess body wash back onto the web as it is turned. After drying to about 16% moisture, the web can be cut into rectangles measuring 11.9 cm×9.0 cm.

A third example of a layered laminate article using a web 1 of the present invention can be a makeup removal pad. The following chemical component shown in Table 2 can be prepared, which is useful for removing makeup. The phase A can be prepared in water at 75° C., which can be the surfactant component for this example. The formula shown does not include the added water. Component phase B can be prepared by mixing the ingredients separately and blending into Phase B at room temperature.

TABLE 2

Chemical component

| Ingredient common name or trade name | Ingredient CTFA name | CAS # | % active chemical added | Phase |
|---|---|---|---|---|
| Carbowax PEG 4600 flake (Dow Chemicals, USA) | Polyethylene Glycol 4600 | 25322-68-3 | 25.8 | B |
| Cocamidopropyl Hydroxysultaine (Stepan) | Cocamidopropyl Hydroxysultaine | 68139-30-0 | 17.3 | A |
| Hamposyl L-30 (Hampshire Chem) | Sodium Lauroyl Sarcosinate | 137-16-6 | 17.3 | A |
| Plantaren 2000 N UP (Cognis Care Chemicals, NJ, USA) | Decyl Glucoside | mixture | 17.3 | A |
| Beta CycloDextrin | Beta CycloDextrin | 7585-39-9 | 7.4 | B |
| Butylene Glycol | Butylene Glycol | 107-88-0 | 5.3 | A |
| Polyox WSR N3000 (Amerchol) | PEG 14M | 25322-68-3 | 2.7 | A |
| Ucare Polymer JR30M (Amerchol) | Polyquaternium-10 | 53568-66-4 | 1.3 | A |
| Perfume | Fragrance | | 1.2 | B |
| D-Panthenol | Panthenol | 81-13-0 | 0.9 | A |
| Salicylic Acid | Salicylic Acid | 69-72-7 | 0.3 | A |
| Menthol | Menthol | 89-78-1 | 0.1 | B |
| Acusol 460N (Rohm & Haas) | Water & Sodium MA/ Diisobutylene Copolymer | | 0.09 | B |
| Misc. preservatives, vitamins | | mixture | QS | A |

An article can be prepared by spraying the surfactant component onto a web 1 of made by any of the processes and variations described herein to an add-on rate of about 150% based on the weight of the web. The article can be stored in a sealed container.

As can be understood from the above description of webs 1 and apparatus 150 of the present invention, many various structures of webs 1 can be made without departing from the scope of the present invention as claimed in the appended claims. For example, webs 1 can be coated or treated with lotions, medicaments, cleaning fluids, anti-bacterial solutions, emulsions, fragrances, surfactants. Likewise, apparatus 150 can be configured to only form tufts 6 on a portion of the web 1, or to form varying sizes or area densities of tufts 6. Additionally, the constituent precursor web(s) 20 can be pretreated or pre-processed to have apertures, embossments, coatings, or the like prior to processing by apparatus 150. For example, a film precursor web 20 can be treated by vacuum forming or hydroforming to be a three-dimensional apertured formed film, as described in any of U.S. Pat. No. 4,609,518, or U.S. Pat. No. 4,629,643, or U.S. Pat. No. 4,695,422, or U.S. Pat. No. 4,839,216, or U.S. Pat. No. 4,342,314, or U.S. Pat. No. 4,463,045.

Further, as can be understood from the above description of webs 1 and apparatus 150 of the present invention, one skilled in the art can recognize that various additional processes known in the art can be combined with the process described to provide various additional structures. For example, prior to entering first nip 116, precursor web(s) 20 can be overbonded with a plurality of weakened melt-stabilized locations which can be incrementally stretched in nip 116 to provide apertures. Such a process is described in U.S. Pat. No. 5,628,097. Further, multiple layers having differing elongation characteristics can be processed in a similar manner as described in US 20030028165A1. In general, any of the known processes commonly referred to as "ring rolling," or "selfing" in the art can be incorporated in apparatus 150 as desired for producing a web 1 for a particular application.

Web 1 may be used for a wide variety of applications, including various filter sheets such as air filter, bag filter, liquid filter, vacuum filter, water drain filter, and bacterial shielding filter; sheets for various electric appliances such as capacitor separator paper, and floppy disk packaging material; various industrial sheets such as tacky adhesive tape base cloth, oil absorbing material, and paper felt; various dry or premoistened wipes such as hard surface cleaning, floor care, and other home care uses, various wiper sheets such as wipers for homes, services and medical treatment, printing roll wiper, wiper for cleaning copying machine, baby wipers, and wiper for optical systems; various medicinal and sanitary sheets, such as surgical gown, medical gowns, wound care, covering cloth, cap, mask, sheet, towel, gauze, base cloth for cataplasm, diaper, diaper liner, diaper cover, feminine napkin covers, feminine napkin or diaper acquisition layer (underneath the cover layer), diaper core, tampon liners, base cloth for adhesive plaster, wet towel, paper towels, tissues; various sheets for clothes, such as padding cloth, pad, jumper liner, and disposable underwear; various life material sheets such as base cloth for artificial leather and synthetic leather, table top, wall paper, blind, wrapping, and packages for drying agents, shopping bag, suit cover, and pillow cover; various agricultural sheets, such as ground covers and erosion control devices, cooling and sun light-shielding cloth, lining curtain, sheet for overall covering, light-shielding sheet, wrapping materials of pesticides, underlining paper of pots for seeding growth; various protection sheets such as fume prevention mask and dust prevention mask, laboratory gown, and dust preventive clothes; various sheets for civil engineering building, such as house wrap, drain material, filtering medium, separation material, overlay, roofing, tuft and carpet base cloth, wall interior material, soundproof or vibration reducing sheet, and curing sheet; and various automobile interior sheets, such as floor mat and trunk mat, molded ceiling material, head rest, and lining cloth, in addition to a separator sheet in alkaline batteries. Other uses include utilizing web 1 as a wipe for personal cleansing or hygiene, such as for a baby wipe, facial cloth or wipe, or body cloth.

In one embodiment, web 1 or a composite comprising web 1 can be utilized as a fecal material storage element. Web 1 can be utilized as a secondary topsheet or sublayer when it is disposed under an apertured web or film to accept and hold low viscosity feces or viscous bodily waste away from a wearer's skin after defecation. Embodiments of the present invention having larger total three dimensional volume within the web or between the tufts generally provide a greater capacity for storage of low viscosity feces. Absorbent articles employing such fecal material storage elements, or sublayers, are described in U.S. Pat. Nos. 5,941,864; 5,957,906; 6,018, 093; 6,010,491; 6,186,992; and 6,414,215, among others.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A fibrous web having a first surface and a second surface, said fibrous web further comprising a first region and at least one discrete second region, the second region being a discontinuity on said second surface and being a tuft comprising a plurality of looped tufted fibers extending from said first surface, said looped tufted fibers defining a distal portion and a proximal portion, said looped tufted fibers generally converging near said proximal portion, said distal portion comprising portions of said looped tufted fibers being bonded together wherein a plurality of bonded portions that are coincident with and substantially aligned along a longitudinal axis of said distal portion are defined.

2. The fibrous web of claim 1, wherein said web comprises a plurality of discrete integral second regions.

3. The fibrous web of claim 2, wherein said plurality of discrete integral second regions is uniformly distributed on said fibrous web.

4. The fibrous web of claim 1, wherein said fibrous web comprises a nonwoven web of substantially randomly oriented fibers.

5. The fibrous web of claim 1, where said fibrous web comprises a nonwoven web having a substantial number of fibers having a predetermined orientation measured as a predetermined angle from the machine direction.

6. The fibrous web of claim 2, wherein said fibers comprise polymers selected from the group consisting of polyethylene, polypropylene, polyester, and blends thereof.

7. The fibrous web of claim 2, wherein said fibers comprise fibers chosen from the group consisting of bicomponent fibers, hollow fibers, non-round fibers, and capillary channel fibers.

8. The fibrous web of claim 1, wherein said fibrous web comprises a laminate of at least two precursor webs.

9. The fibrous web of claim 8, wherein a said laminate comprises a polymer film.

10. A fibrous web having a first surface and a second surface, said fibrous web further comprising a first region and a plurality of discrete second regions, each said second region comprising a discontinuity on said second surface and a tuft comprising a plurality of looped tufted fibers integral with but extending from said first surface, said looped tufted fibers defining a distal portion and a proximal portion, said looped tufted fibers, generally converging near said proximal portion, said second surface having thereon a plurality of bonded regions in the form of stripes or bands of melt-bonded regions.

11. The fibrous web of claim 10, wherein at least some of said stripes or bands of melt-bonded regions are discontinuous.

12. The fibrous web of claim 10, wherein said fibers comprise polymers selected from the group consisting of polyethylene, polypropylene, polyester, and blends thereof.

13. The fibrous web of claim 10, wherein said fibers comprise fibers chosen from the group consisting of bicomponent fibers, hollow fibers, non-round fibers, and capillary channel fibers.

14. The fibrous web of claim 10, wherein said fibrous web comprises a laminate of at least two precursor webs.

15. The fibrous web of claim 14, wherein said laminate comprises a polymer film.

16. A fibrous web having a first surface and a second surface, said fibrous web further comprising a first region and a plurality of discrete second regions, each said second region comprising a discontinuity on said second surface and a tuft comprising a plurality of looped tufted fibers integral with but extending from said first surface, said looped tufted fibers defining a distal portion and a proximal portion, said looped tufted fibers, generally converging near said proximal portion, said distal portion comprising portions of said looped tufted fibers being bonded together to define a bonded area that extends along a longitudinal axis of said tuft, and wherein said second surface comprises thereon a plurality of non-intersecting, substantially continuous bonded regions.

17. The fibrous web of claim 16, wherein said fibers comprise polymers selected from the group consisting of polyethylene, polypropylene, polyester, and blends thereof.

18. The fibrous web of claim 16, wherein said fibers comprise fibers chosen from the group consisting of bicomponent fibers, hollow fibers, non-round fibers, and capillary channel fibers.

19. The fibrous web of claim 16, wherein said bonded area comprises adhesive-bonded portions.

20. The fibrous web of claim 16, wherein said bonded area comprises distally-disposed melt-bonded portions.

21. A disposable absorbent article, the article having at least one component comprising a fibrous web comprising a first region and a plurality of discrete integral second regions, the second regions having at least one portion being a region of fiber discontinuity and at least another portion being a tuft comprising a plurality of looped tufted fibers integral with but extending from the first region, wherein said web comprises bonded regions on distal portions of said tufts, wherein each of said bonded regions comprises a plurality of adjacent fiber bonds that are coincident with and substantially aligned along a longitudinal axis of said distal portion, and wherein said looped tufted fibers generally converge near a proximal portion of said tufts.

22. The article of claim 21, wherein said article is selected from the group consisting of a catamenial article, a tampon, an incontinence article, and a diaper.

23. A multilayer tufted web comprising at least a first and second precursor webs, said multilayer fibrous web further comprising a first surface and a second surface, and a first region and a plurality of discrete integral second regions, the second regions having at least one portion being a region of fiber discontinuity and at least another portion being a tuft comprising a plurality of looped tufted fibers integral with but extending from the first surface, wherein the looped tufted fibers comprise fibers from at least one of said first or second precursor webs, and said looped tufted fibers defining a distal portion and a proximal portion, said looped tufted fibers generally converging near said proximal portion, said distal portion comprising portions of said looped tufted fibers being bonded together to define a bonded area that extends along a longitudinal axis of said tuft.

24. The fibrous web of claim 23, wherein said first and second precursor webs each comprise a nonwoven web of substantially randomly oriented fibers.

25. The fibrous web of claim 23, wherein one of said first or second precursor webs comprise a polymer film web.

26. A multilayer tufted web comprising first and second precursor webs joined together to form a laminate having first and second opposed outwardly facing surfaces, said first precursor web comprising a nonwoven having looped tufted fibers facing outwardly from said first surface and being bonded together to define a bonded area that extends along a longitudinal axis of said tuft, said looped tufted fibers defining a distal portion and a proximal portion, said looped tufted fibers generally converging near said proximal portion, said second precursor web comprising cellulose.

27. A multilayer tufted web according to claim 26 further comprising a third precursor web, wherein said second precursor web is positioned between said first and third precursor webs to form a laminate.

28. A multilayer tufted web according to claim 27, wherein said second precursor web comprises tissue grade paper.

29. A multilayer tufted web according to claim 28, wherein said second precursor web further comprises thermoplastic fibers.

30. A multilayer tufted web according to claim 28, wherein said third precursor web comprises a polymer film.

31. A fibrous web comprising a first surface; an opposing second surface; a web body disposed between said first surface and said second surface; a tuft extending from said first surface; wherein said tuft comprises fibers that have been repositioned from within said web body to a position extending from said first surface; wherein a plurality of bonds exist at distal portions of adjacent fibers associated with said tuft, and wherein said plurality of bonds are substantially aligned with one another to define a bond region.

32. The fibrous web of claim 31, further comprising a second bond region associated with said second surface, said second bond region in the form of stripes or bands.

* * * * *